(12) United States Patent
Tachikawa

(10) Patent No.: US 7,706,505 B2
(45) Date of Patent: Apr. 27, 2010

(54) WIRELESS X-RAY FLUOROSCOPIC IMAGING SYSTEM, INTER-UNIT SYNCHRONIZATION METHOD OF THE SAME, AND COMPUTER PROGRAM

(75) Inventor: Hirohide Tachikawa, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/362,001

(22) Filed: Jan. 29, 2009

(65) Prior Publication Data

US 2009/0201841 A1    Aug. 13, 2009

(30) Foreign Application Priority Data

Feb. 8, 2008  (JP) .............................. 2008-029588

(51) Int. Cl.
*H05G 1/08* (2006.01)
(52) U.S. Cl. ..................... 378/98.8; 378/42; 378/98.2
(58) Field of Classification Search .............. 378/42, 378/91, 98, 98.2, 98.5, 98.8, 210
See application file for complete search history.

(56) References Cited

U.S. PATENT DOCUMENTS 7,508,915 B2 * 3/2009 Amitani et al. ............ 378/98.8

2004/0258204 A1 * 12/2004 Nokita et al. ................. 378/91
2009/0060136 A1 * 3/2009 Tamakoshi .................... 378/91

FOREIGN PATENT DOCUMENTS

JP    2006-305106    11/2006

* cited by examiner

*Primary Examiner*—Hoon Song
(74) *Attorney, Agent, or Firm*—Cowan, Liebowitz & Latman, P.C.

(57) ABSTRACT

A wireless X-ray fluoroscopic imaging system is provided. The system includes an X-ray generation unit configured to perform X-ray exposure for each frame of imaging; a sensor unit configured to output image data; and an image processing unit configured to designate the exposure, wherein the sensor unit includes a first counter configured to be reset and resume counting in response to a beacon signal, and a unit configured to save a readout trigger offset for readout, and starts the readout when a counter value of the first counter matches the readout trigger offset, and the image processing unit includes a second counter configured to be reset and resume counting in response to the beacon signal, and a unit configured to save an exposure trigger offset for the exposure, and starts the exposure when a counter value of the second counter matches the exposure trigger offset.

11 Claims, 27 Drawing Sheets

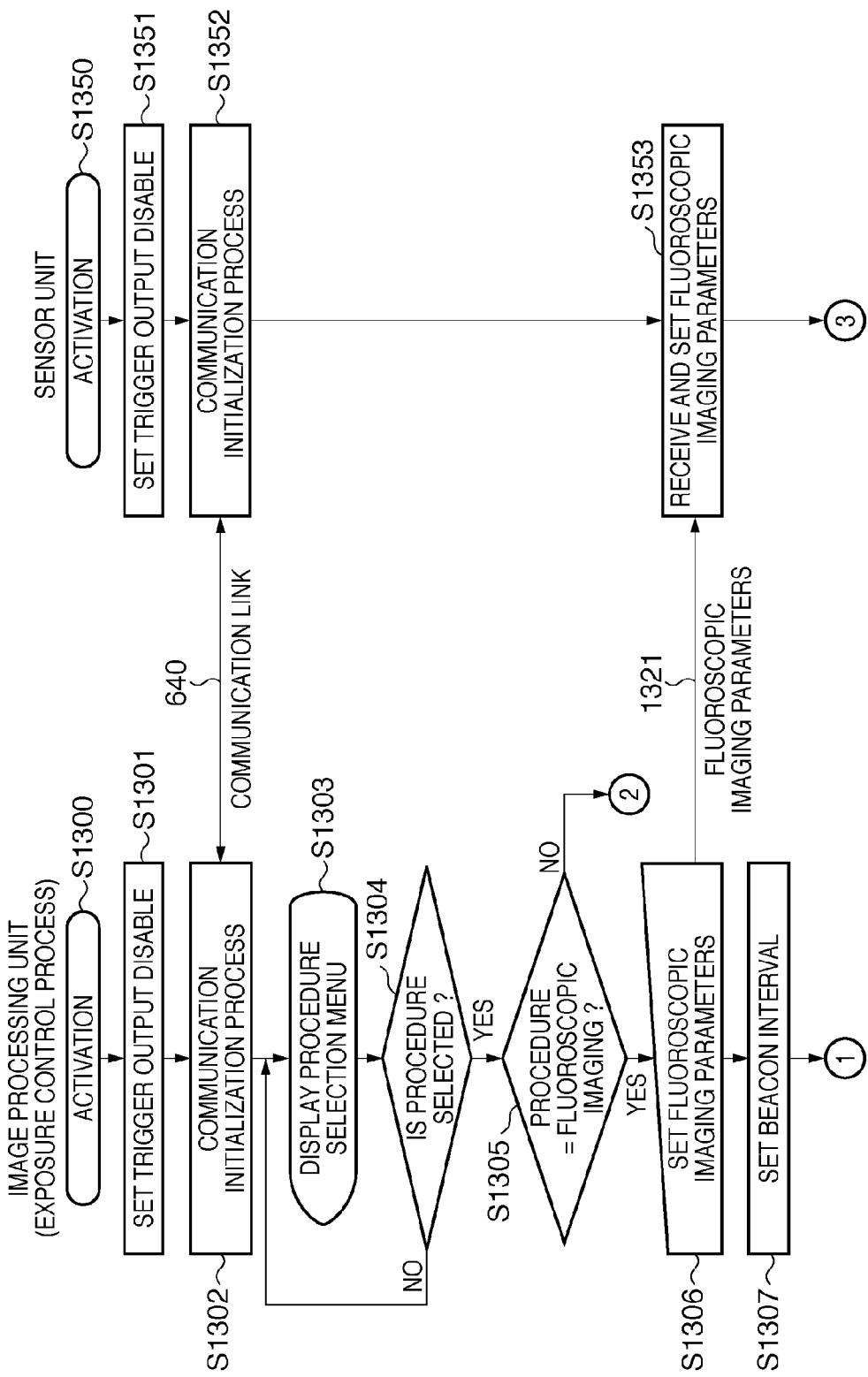

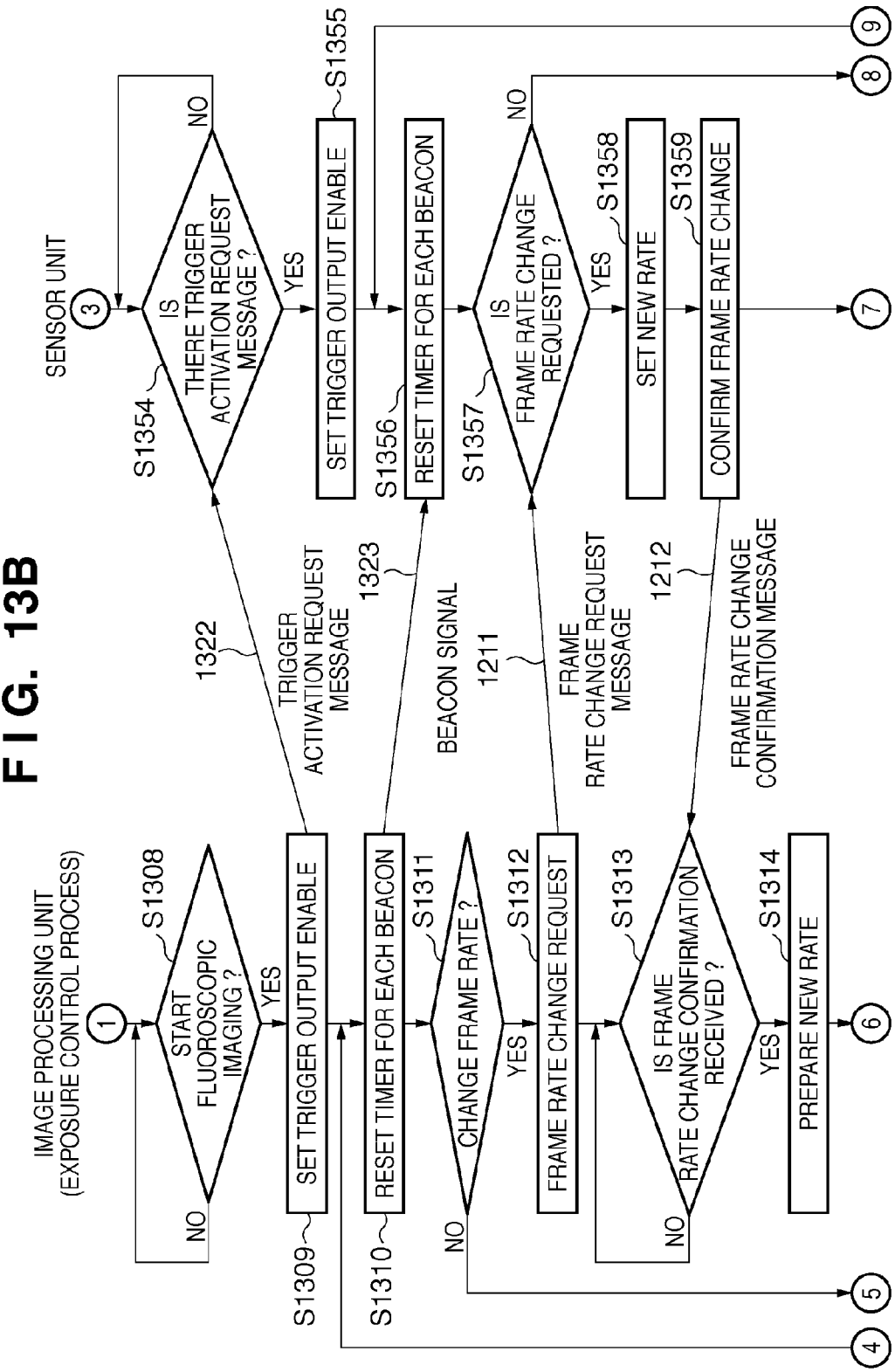

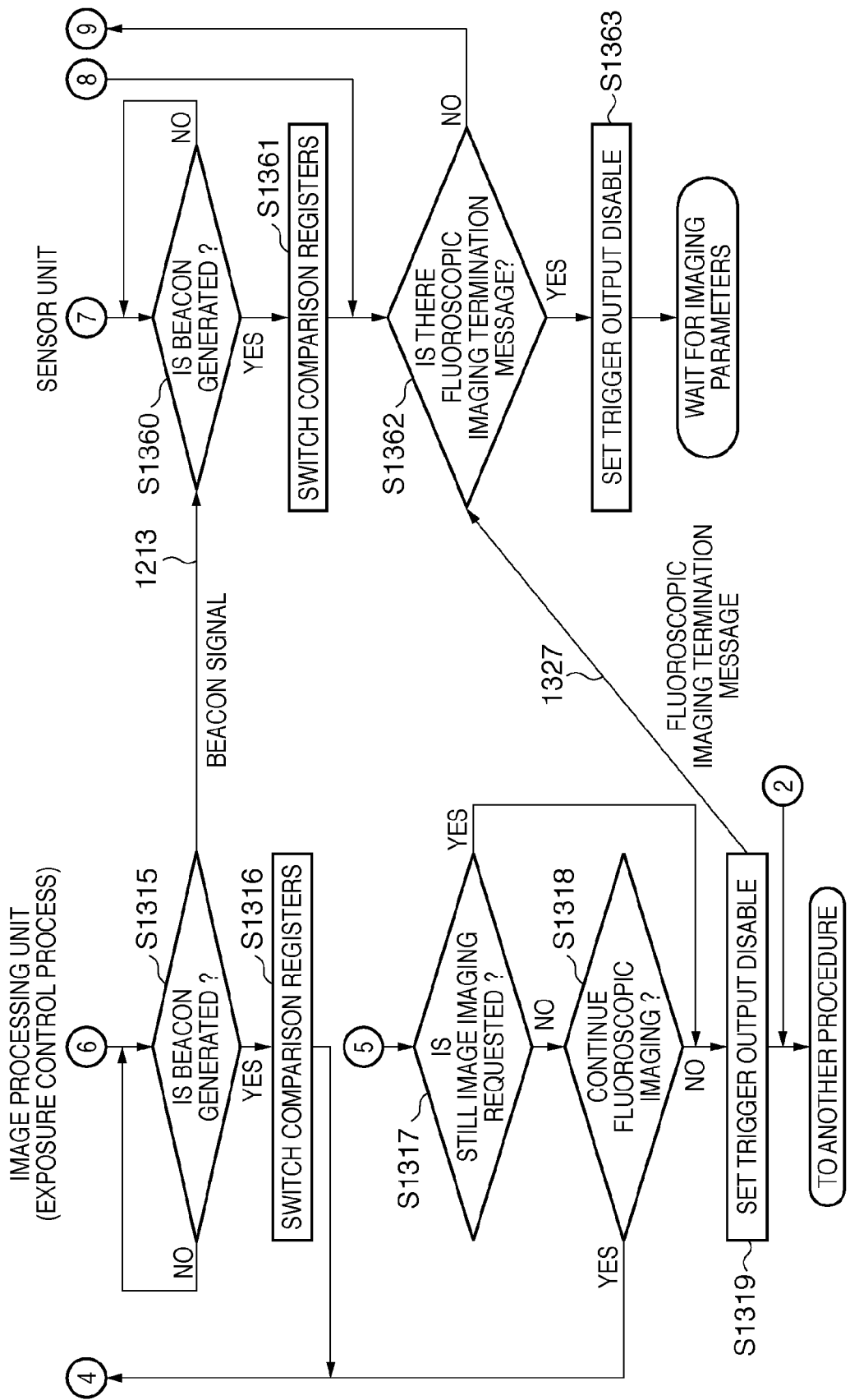

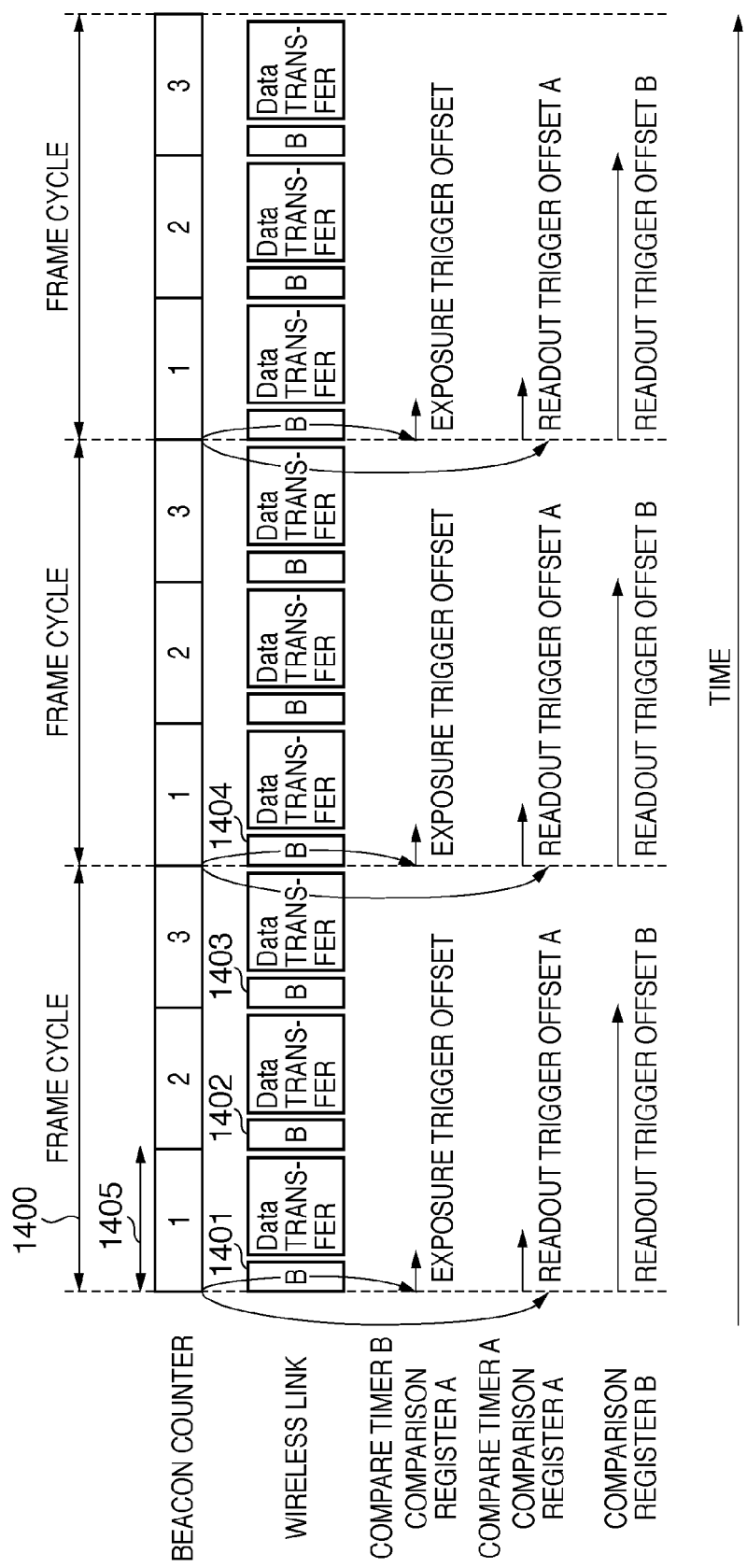

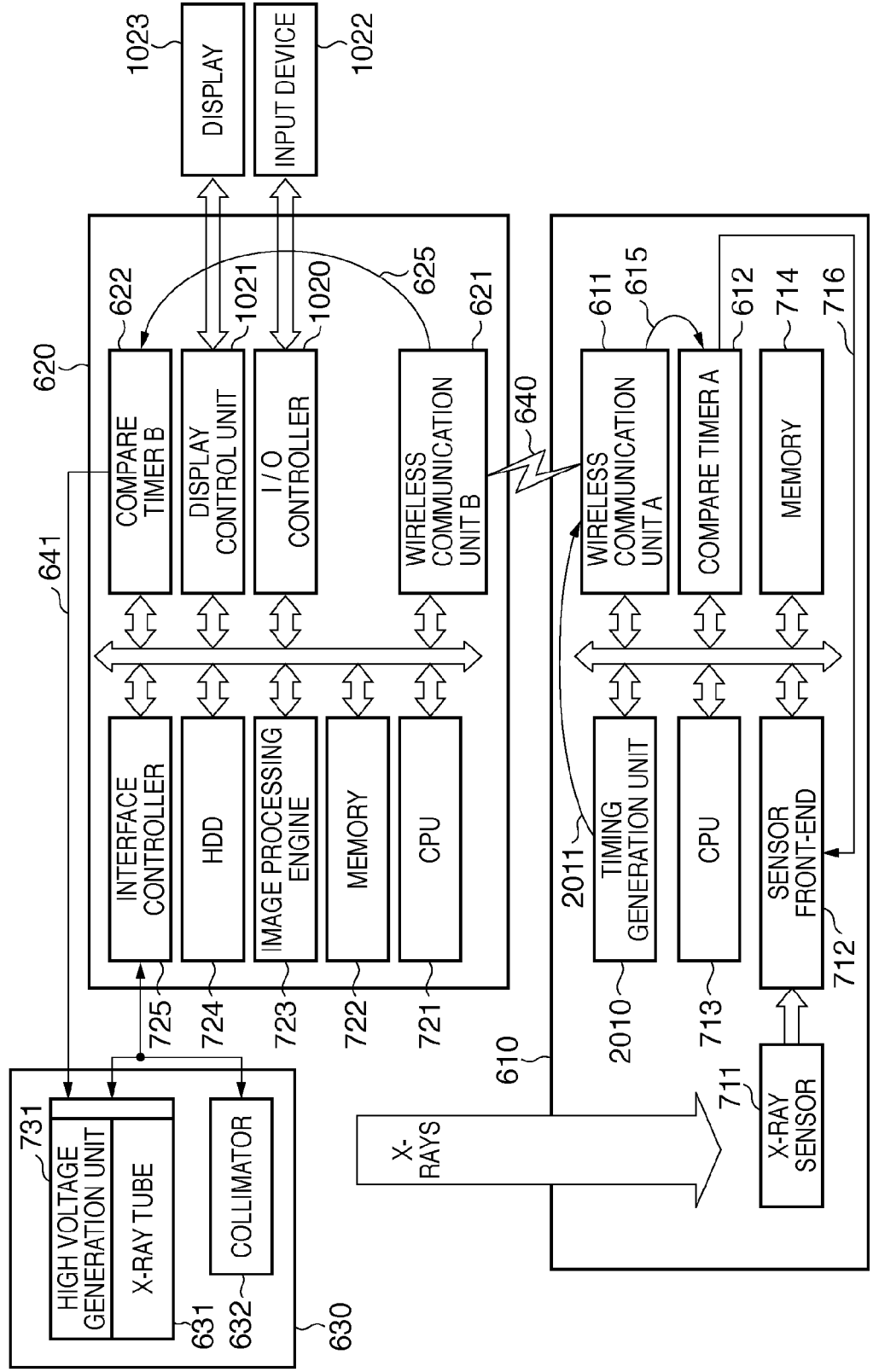

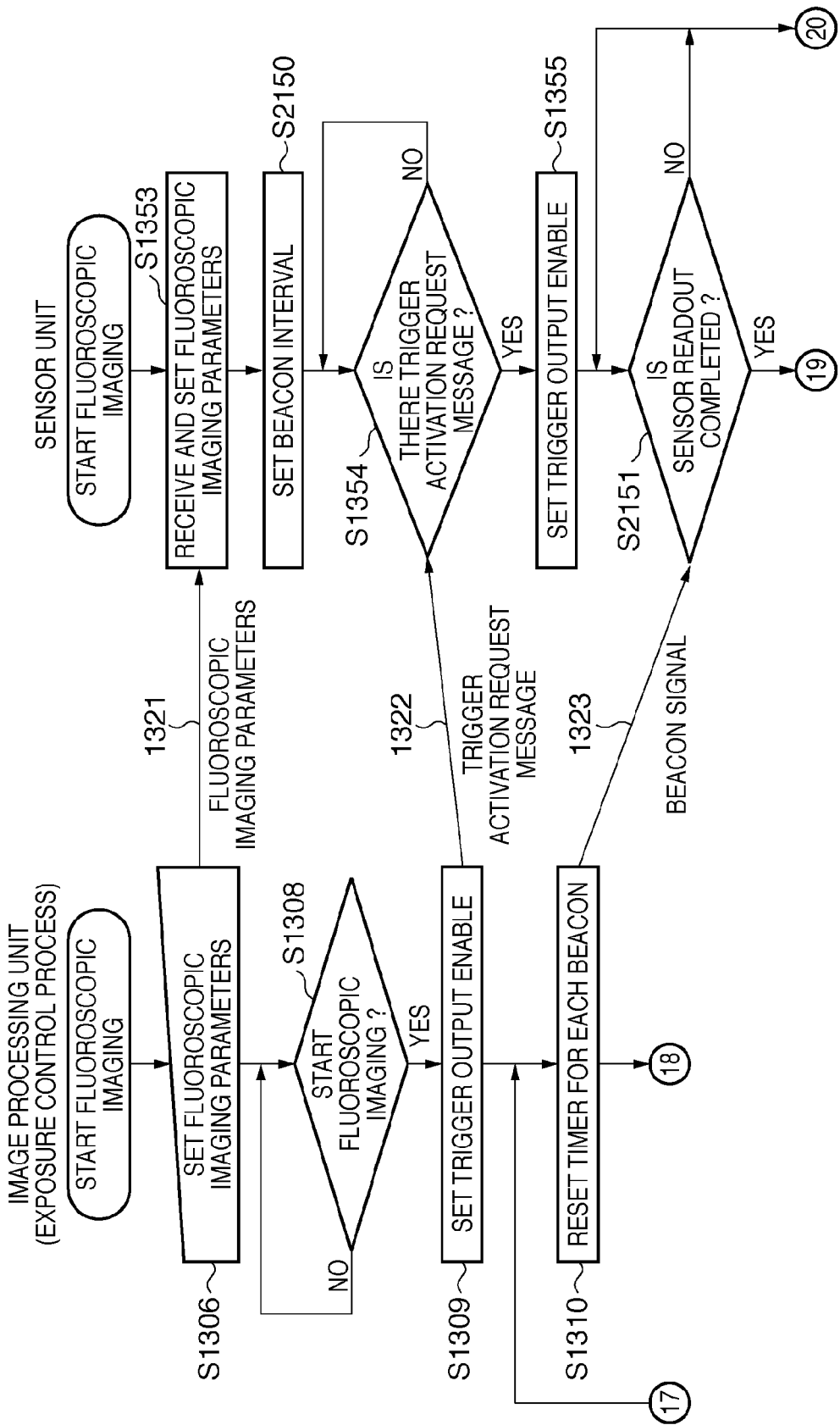

WIRELESS X-RAY FLUOROSCOPIC IMAGING SYSTEM, INTER-UNIT SYNCHRONIZATION METHOD OF THE SAME, AND COMPUTER PROGRAM

BACKGROUND OF THE INVENTION

1. Field of the Invention

The present invention relates to an X-ray fluoroscopic imaging system in which a sensor unit is physically separable, an inter-unit synchronization method of the same, and a computer program.

2. Description of the Related Art

Attempts have been made to improve the handling ability of a sensor unit of an X-ray imaging system by giving a physically separable unit construction to the sensor unit, thereby improving the user-friendliness of the system. X-ray imaging is classified into X-ray fluoroscopic imaging and X-ray still image imaging. In X-ray fluoroscopic imaging, radiography is performed frame by frame.

FIG. 1 shows an example of the configuration of an X-ray imaging system in which a sensor unit is physically separated. FIG. 1 is a view for explaining an example of the X-ray imaging system in which a sensor unit is separated. This X-ray imaging system includes a sensor unit 110, image processing unit 120, and X-ray generation unit 130.

The sensor unit 110 is physically separable from other units.

The image processing unit 120 includes a timing generation unit 121, and performs image processing on a radiographed image transmitted from the sensor unit 110. The timing generation unit 121 generates a trigger signal for performing synchronization control on the sensor unit 110 and X-ray generation unit 130.

The X-ray generation unit 130 includes an X-ray tube 131 and collimator 132. The X-ray generation unit 130 generates X-rays, and exposes the sensor unit 110 to the X-rays. The X-ray tube 131 generates X-rays for the X-ray exposure. The collimator 132 adjusts the X-rays for exposure.

The case where image data is read out from the sensor only once for every X-ray exposure will be explained below with reference to FIG. 2. FIG. 2 is an example of a timing chart of exposure and readout when using a CMOS sensor. X-ray exposure 201 is made active by an exposure trigger 200 transmitted to the X-ray generation unit 130, and readout 203 is started by a readout trigger 202. Since a delay time is necessary from the start of X-ray exposure to the start of readout from the sensor, the readout trigger 202 has a predetermined offset 204 from the exposure trigger. Also, a predetermined time is necessary before readout is completed. Therefore, no accurate image data can be read out if the next X-ray exposure is started before readout is completed. Accordingly, a time 205 from the completion of readout from the sensor to the start of the next X-ray exposure must be positive.

The case where readout is performed twice for every X-ray exposure will be explained below with reference to FIG. 3. FIG. 3 is an example of a timing chart of exposure and readout when using a LANMIT sensor. When using the LANMIT sensor, X-ray intensity distribution information is calculated for each frame by subtracting charge distribution information when no X-rays are applied from that immediately after X-rays are applied. Therefore, readout must be performed twice.

As in the case explained with reference to FIG. 2, a time 300 from the completion of the second readout to the start of the next X-ray exposure must be positive in this case as well.

As explained above, even in the arrangement in which the sensor unit 110 is physically separable as shown in FIG. 1, the X-ray generation unit 130 and sensor unit 110 must operate in strict synchronism with each other. To meet this demand, trigger signal transmission using a dedicated signal line 140 as shown in FIG. 1 is performed in the X-ray imaging system in which the sensor unit 110 is separable.

The merit, however, of the X-ray imaging system in which the sensor unit 110 is separable is that the portability of the sensor unit 110 improves and imaging can be performed by setting the sensor unit 110 in various positions. From this point of view, the sensor unit 110 is desirably completely wireless. To make the sensor unit 110 wireless, how to handle the power supply and large-volume image data is a problem. However, the largest problem is how to wirelessly synchronize the sensor unit 110 and X-ray generation unit 130 as described above.

Examples of protocols normally used in wireless communication are IEEE802.11 (wireless LAN) and IEEE802.15.3 (UWB). In wireless communications using these protocols, data communication can be performed in a constructed network by using a packet containing a header and payload. However, it is difficult to establish synchronization by defining a dedicated packet on a communication protocol of, for example, a wireless LAN. This is so because the necessary arbitration time is uncertain in CSMA/CA (Carrier Sense Multiple Access with Collision Avoidance) as a best effort type access control scheme that is a general wireless communication protocol.

On the other hand, a quality priority communication method taking account of Quality of Service (QoS) using the TDMA (Time Division Multiple Access) scheme instead of the CSMA/CA scheme is also defined in a wireless communication protocol. FIG. 4 shows an example of the configuration of a super frame 400 as a communication unit of IEEE802.15.3 as a wireless communication standard using the TDMA scheme. As shown in FIG. 4, this wireless communication standard performs wireless communication by repeating the super frame 400. In the structure of a super frame 400 #m, a beacon 401 #m contains time allocation information of constituent elements (Contention access period, MCTA, and CTA) in the super frame 400 #m.

A node having received the beacon 401 counts the preferential communication enable period (MCTA) allocated to the node in units of µsec by using an internal timer, and performs QoS communication at the designated time. The time required for wireless arbitration can be shortened by thus performing QoS communication.

Even when the arbitration time is unlimitedly shortened, however, it is necessary by analyzing the protocol to extract actual timing information contained in the payload from a wirelessly communicated wireless packet. A delay occurs when using the extracted timing information as a trigger signal. This time loss caused by the protocol analysis is also a factor that makes synchronization by wireless packets difficult.

Japanese Patent Laid-Open No. 2006-305106 describes a method of synchronizing the sensor unit 110 and X-ray generation unit 130 in a wireless environment in which the two units are physically separated. In this method, the separated units each contain an internal timer, the two timers are synchronized through a wired signal line before the two units are separated, and the two units are synchronized on the basis of the values of the internal timers after the units are separated.

There is also an arrangement as shown in FIG. 5. FIG. 5 shows an example of the system configuration of a wireless X-ray imaging system. The same reference numerals as in FIG. 1 denote the same parts in FIG. 5, and a repetitive explanation will be omitted. This configuration includes a second wireless link 501 dedicated for synchronization in addition to a wireless link 500 for data communication. The second wireless link 501 requires no communication arbitration and only a short protocol analyzing time. Trigger signals are transmitted by using the dedicated wireless link 501.

When using the method described in Japanese Patent Laid-Open No. 2006-305106, however, an error occurs between the internal timers of the two units with the elapse of time, and this makes synchronization impossible. In addition, the method using the additional wireless link dedicated for synchronization increases the cost.

Accordingly, the present invention provides a wireless X-ray fluoroscopic imaging system that can be used with a configuration using a single wireless link, and reduces synchronization errors between units.

SUMMARY OF THE INVENTION

According to one aspect of the present invention, there is provided a wireless X-ray fluoroscopic imaging system comprising: an X-ray generation unit configured to perform X-ray exposure for each frame of fluoroscopic imaging; a sensor unit including a sensor configured to convert X-rays of the X-ray exposure into charge distribution information and output the information as image data; and an image processing unit configured to designate the exposure by the X-ray generation unit, and receive the image data from the sensor unit, wherein the sensor unit and the image processing unit communicate with each other via a wireless link, the sensor unit includes a first counter configured to be reset and resume counting in response to a beacon signal communicated via the wireless link, and a unit configured to save a counter value corresponding to a readout trigger offset which defines a time from start of the frame to start of readout of the image data, and starts the readout when a counter value of the first counter matches the saved counter value corresponding to the readout trigger offset, and transfers the readout image data to the image processing unit via the wireless link, and the image processing unit includes a second counter configured to be reset and resume counting in response to the beacon signal of the wireless link, and a unit configured to save a counter value corresponding to an exposure trigger offset which defines a time from start of the frame to start of the exposure, and starts the exposure when a counter value of the second counter matches the saved counter value corresponding to the exposure trigger offset.

According to another aspect of the present invention, there is provided an inter-unit synchronization method in a wireless X-ray fluoroscopic imaging system comprising: an X-ray generation unit configured to perform X-ray exposure for each frame of fluoroscopic imaging; a sensor unit including a sensor configured to convert X-rays of the X-ray exposure into charge distribution information and output the information as image data; and an image processing unit configured to designate the exposure by the X-ray generation unit, and receive the image data from the sensor unit, the sensor unit and the image processing unit communicating with each other via a wireless link, wherein the sensor unit includes a first counter configured to be reset and resume counting in response to a beacon signal communicated by the wireless link, and save a counter value corresponding to a readout trigger offset which defines a time from the frame to start of readout of the image data, and starts the readout when a counter value of the first counter matches the saved counter value corresponding to the readout trigger offset, and transfers the readout image data to the image processing unit via the wireless link, and the image processing unit includes a second counter configured to be reset and resume counting in response to the beacon signal of the wireless link, and saves a counter value corresponding to an exposure trigger offset which defines a time from start of the frame to start of the exposure, and the X-ray generation unit starts the exposure when a counter value of the second counter matches the saved counter value corresponding to the exposure trigger offset.

Further features of the present invention will become apparent from the following description of exemplary embodiments with reference to the attached drawings.

BRIEF DESCRIPTION OF THE DRAWINGS

FIGS. 13A to 13C are flowcharts for explaining an example of the process of switching frame rates according to the second embodiment of the present invention;

FIG. 14 is an example of a timing sequence diagram according to the third embodiment of the present invention;

FIG. 20 is an example of a system block diagram according to the sixth embodiment of the present invention; and FIGS. 21A to 21C are an example of a flowchart according to the sixth embodiment of the present invention.

DESCRIPTION OF THE EMBODIMENTS

Embodiments of a wireless X-ray fluoroscopic imaging system according to the present invention will be explained below with reference to the accompanying drawings. Note that X-ray fluoroscopic imaging will be simply expressed as fluoroscopic imaging hereinafter.

First Embodiment

Figure 6:
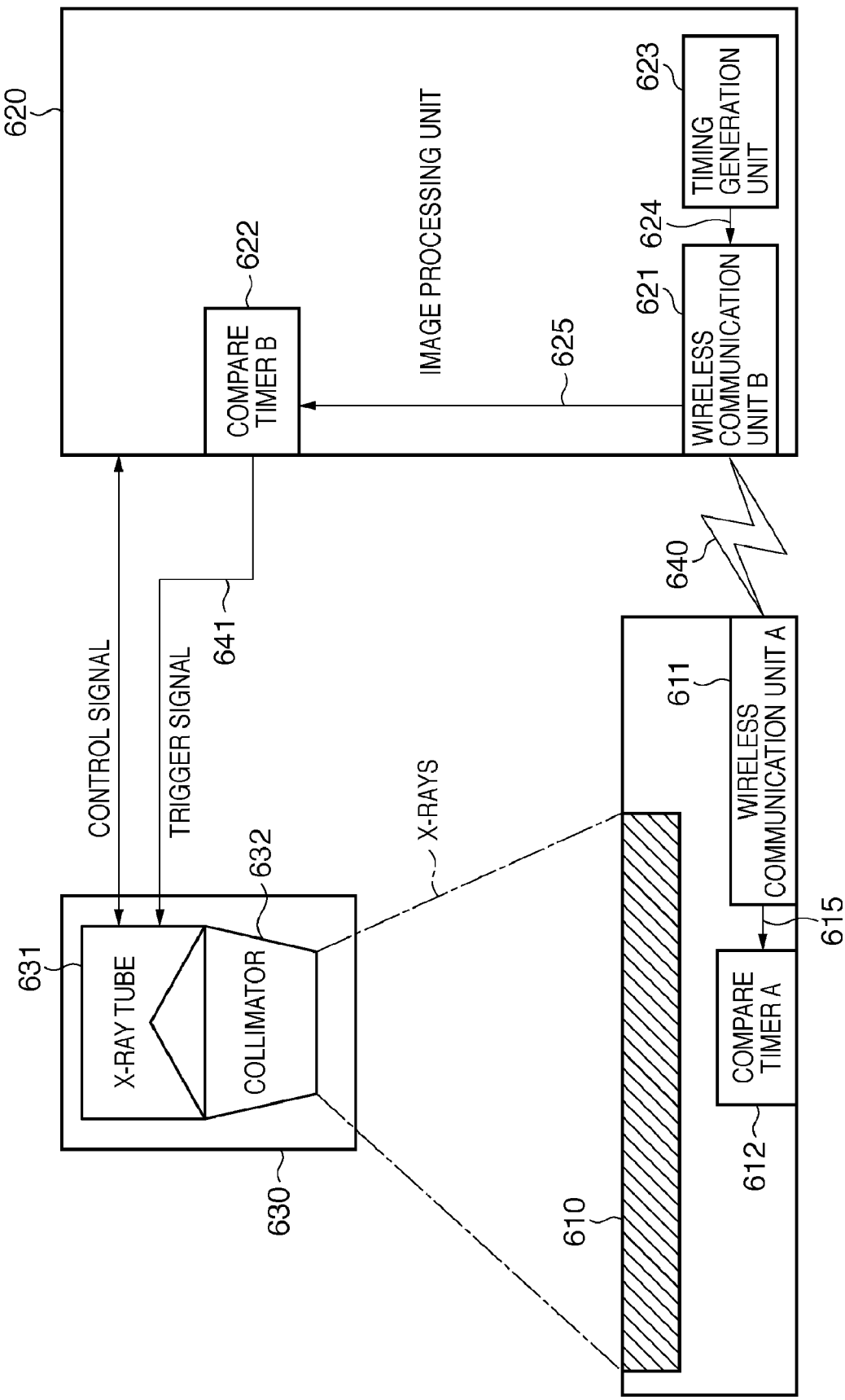
FIG. 6 is an example of a system block diagram for explaining an outline of the first embodiment of the present invention.

An outline of this embodiment will be explained below with reference to FIG. 6. FIG. 6 is an example of a system block diagram for explaining the outline of the first embodiment of the present invention.

An X-ray fluoroscopic imaging system according to the present invention includes a sensor unit 610 physically separated from other units, and an image processing unit 620 including an X-ray generation unit 630 required operating in synchronism with the sensor unit 610.

The sensor unit 610 has a wireless communication unit A 611 and compare timer A 612. The compare time A 612 generates a readout trigger. This readout trigger initiates readout from the sensor.

The image processing unit 620 includes a wireless communication unit B 621, compare timer B 622, and timing generation unit 623. The compare timer B 622 generates an exposure trigger for an X-ray tube 631. This exposure trigger initiates X-ray exposure. The timing generation unit 623 generates a timing signal 624 for controlling synchronization between the sensor unit 610 and X-ray generation unit 630.

A wireless link 640 such as IEEE802.11 or IEEE802.15.3 is established between the sensor unit 610 and image processing unit 620. Radiographed image data and the like are communicated through the wireless link 640. In this embodiment, the wireless communication unit B 621 functions as an access point (AP) of IEEE802.11 or a piconet coordinator (PNC) of IEEE802.15.3. However, the wireless communication unit A 611 or another wireless communication device (not shown) may also function as the AP or PNC. The case where the wireless communication unit A 611 functions as the AP or PNC will be explained later in the sixth embodiment.

The AP or PNC periodically transmits a beacon signal. In this embodiment, the wireless communication unit B 621 transmits a beacon signal in response to the reception of the timing signal 624 generated by the timing generation unit 623.

The X-ray generation unit 630 includes the X-ray tube 631 and a collimator 632. The X-ray generation unit 630 generates X-rays, and exposes the sensor unit 610 to the X-rays. The X-ray tube 631 generates radiation for the X-ray exposure. The collimator 632 adjusts the radiation for the exposure.

First, the operation of the image processing unit 620 will be explained below. The wireless communication unit B 621 having received the timing signal 624 transmits a beacon signal, and sends a compare timer B reset signal 625 to the compare timer B 622 connected by a wired signal line. The compare timer B 622 resets the counter value upon receiving the compare timer B reset signal, and resumes count-up. A counter value from the reset of the compare timer B 622 to the transmission of an exposure trigger signal 641 is preset in the compare timer B 622. When the counter value of the compare timer B 622 matches the preset counter value, the compare timer B 622 sends the exposure trigger signal 641 to the X-ray tube 631. Accordingly, X-ray exposure can be started when a predetermined time has elapsed since the beacon signal is transmitted. The continuation time of exposure is, for example, 10 msec.

Next, the operation of the sensor unit 610 will be explained. The wireless communication unit A 611 having received the beacon signal sends a compare timer A reset signal 615 to the compare timer A 612 immediately after the reception of the beacon signal. The compare timer A 612 resets the counter value upon receiving the compare timer A reset signal 615, and resumes count-up. A counter value before the transmission of a readout trigger signal is preset in the compare timer A 612. When the counter value of the compare timer A 612 matches the preset counter value, the compare timer A 612 sends the readout trigger signal. Accordingly, readout from the sensor can be started when a predetermined time has elapsed since the beacon signal is transmitted.

As described above, the first counter in the sensor unit 610 and the second counter in the image processing unit 620 are simultaneously reset at the same time the beacon signal is transmitted. Therefore, the two units can be synchronized whenever the beacon signal is transmitted. Also, a frame is started by using the transmission of the beacon signal as a trigger. Accordingly, fluoroscopic imaging can be performed in a desired frame cycle by matching the communication interval of the beacon signal with the frame cycle of fluoroscopic imaging.

Details of the operation briefly described above will be explained below with reference to FIGS. 7 to 9. First, each drawing will be explained.

Figure 7:
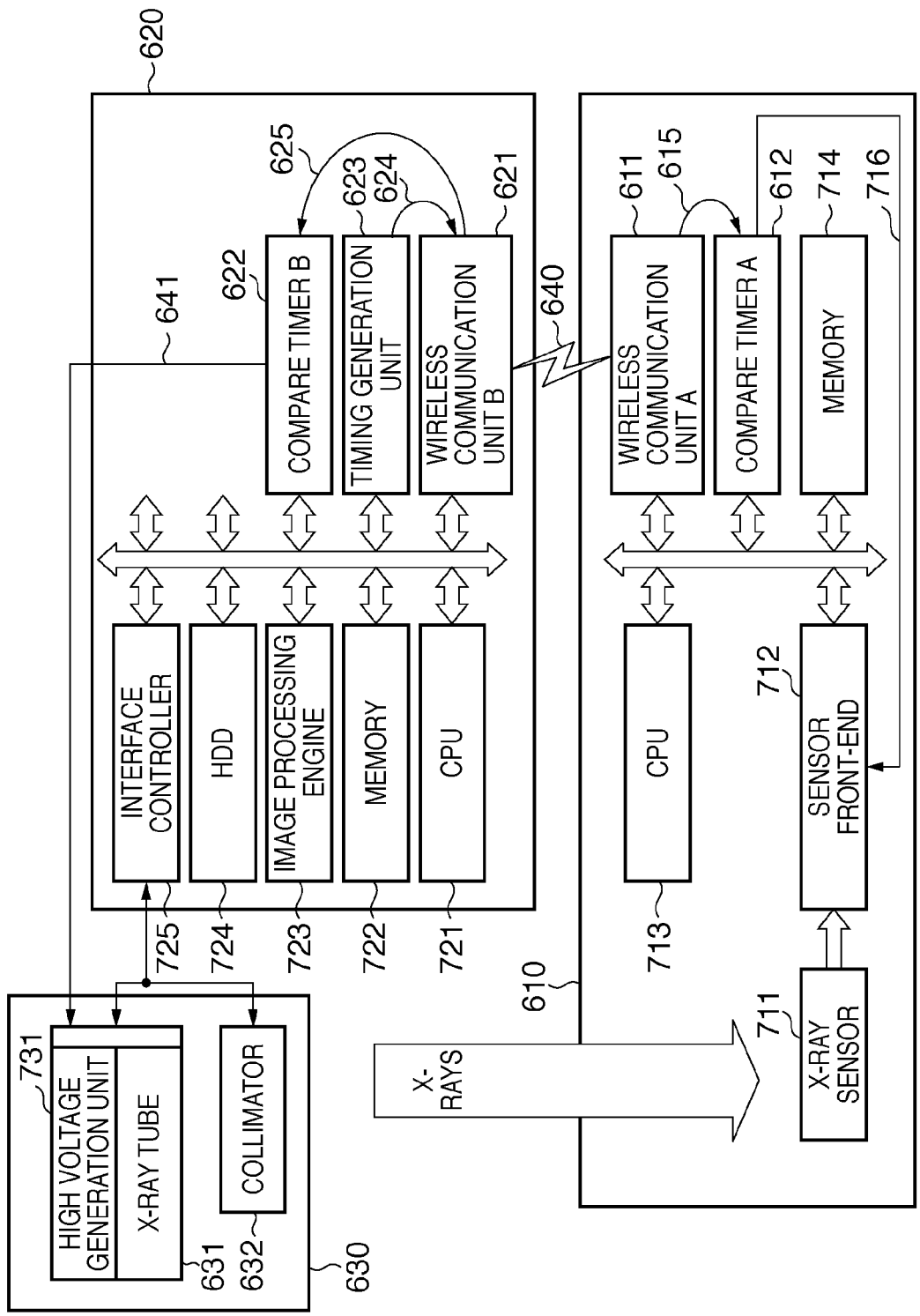
FIG. 7 is an example of a system block diagram according to the first embodiment of the present invention.

FIG. 7 is an example of a detailed system block diagram of the X-ray fluoroscopic imaging system according to this embodiment. The same reference numerals as in FIG. 6 denote the same parts in FIG. 7, and a repetitive explanation will be omitted.

In addition to the constituent elements explained with reference to FIG. 6, the sensor unit 610 further includes an X-ray sensor 711, front-end 712, CPU 713, and memory 714. The X-ray sensor 711 converts X-ray intensity distribution information in each area on a panel into digital information by using a photoelectric conversion element. The front-end 712 receives a readout trigger signal 716 and performs the process of sequentially reading out data from the X-ray sensor 711. The CPU 713 controls the sensor unit 610. The memory 714 stores the data read out from the X-ray sensor 711.

In addition to the constituent elements explained with reference to FIG. 6, the image processing unit 620 further includes a CPU 721, memory 722, image processing engine 723, HDD 724, and interface controller 725.

The CPU 721 controls the image processing unit 620. The memory 722 is used as a work memory of the CPU 721 or image processing unit 620. The image processing engine 723 assists image processing in a hardware manner. The HDD 724 is a secondary memory device for storing image data. The interface controller 725 is, for example, a controller area network (CAN) that allows the image processing unit 620 to control external apparatuses.

The X-ray generation unit 630 further includes a high voltage generation unit 731 in addition to the constituent elements explained with reference to FIG. 6. The high voltage generation unit 731 generates a high voltage for X-ray exposure.

Figure 8:
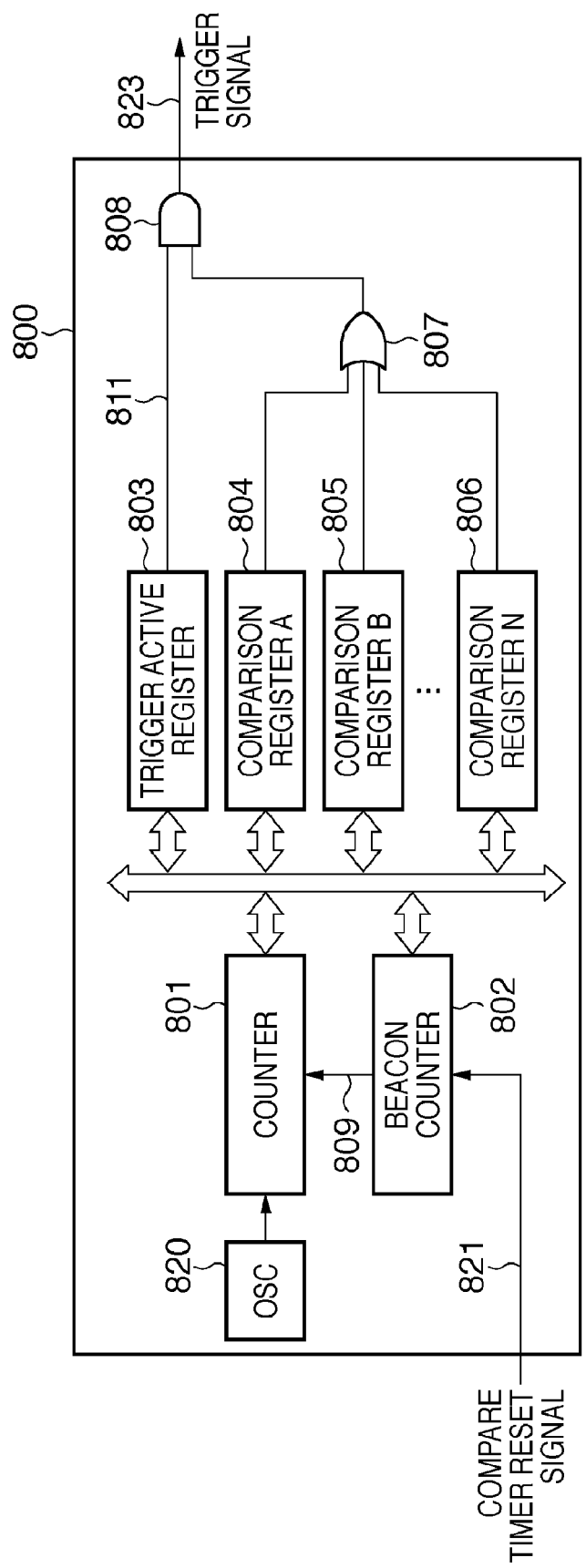
FIG. 8 is an example of an internal block diagram of a compare timer according to the first embodiment of the present invention.

FIG. 8 is an example of an internal block diagram of a compare timer 800. The compare timers A 612 and B 622 also have the configuration shown in FIG. 8.

The compare timer 800 includes a counter 801, beacon counter 802, trigger active register 803, comparison register A 804, comparison register B 805, . . . , comparison register N 806, and oscillator (OSC) 820.

The oscillator 820 generates a clock at a predetermined interval. The counter 801 counts the clock output from the oscillator 820. The beacon counter 802 receives a compare timer reset signal 821, and performs control to determine whether to output a counter reset signal 809 to the counter 801. The compare timer reset signal 821 corresponds to the compare timer A reset signal 615 or compare timer B reset signal 625. The trigger active register 803 is used to set whether to permit a trigger output from the compare timer 800.

When permitting the trigger output, "trigger output enable" is set, and a trigger signal permit output 811 is output. When inhibiting the trigger output, "trigger output disable" is set, and nothing is output. Each of the comparison registers A 804, B 805, and N 806 compares a counter value preset in the register with the counter value of the counter 801. If the two values match, the corresponding comparison register outputs a one-shot pulse output. An OR gate 807 ORs the one-shot pulse outputs from the comparison registers.

Accordingly, if at least one of the comparison registers outputs the one-shot pulse output, the OR gate 807 also outputs the one-shot pulse output. An AND gate 808 ANDs the one-shot pulse output from the OR gate 807 and the trigger signal prohibit output 811, and outputs a trigger signal 823 on the basis of the logical product. Therefore, the AND gate 808 does not output the trigger signal 823 as long as the trigger active register 803 is set to "trigger output disable". The trigger signal 823 corresponds to the exposure trigger signal 641 or readout trigger signal 716.

Figure 9:
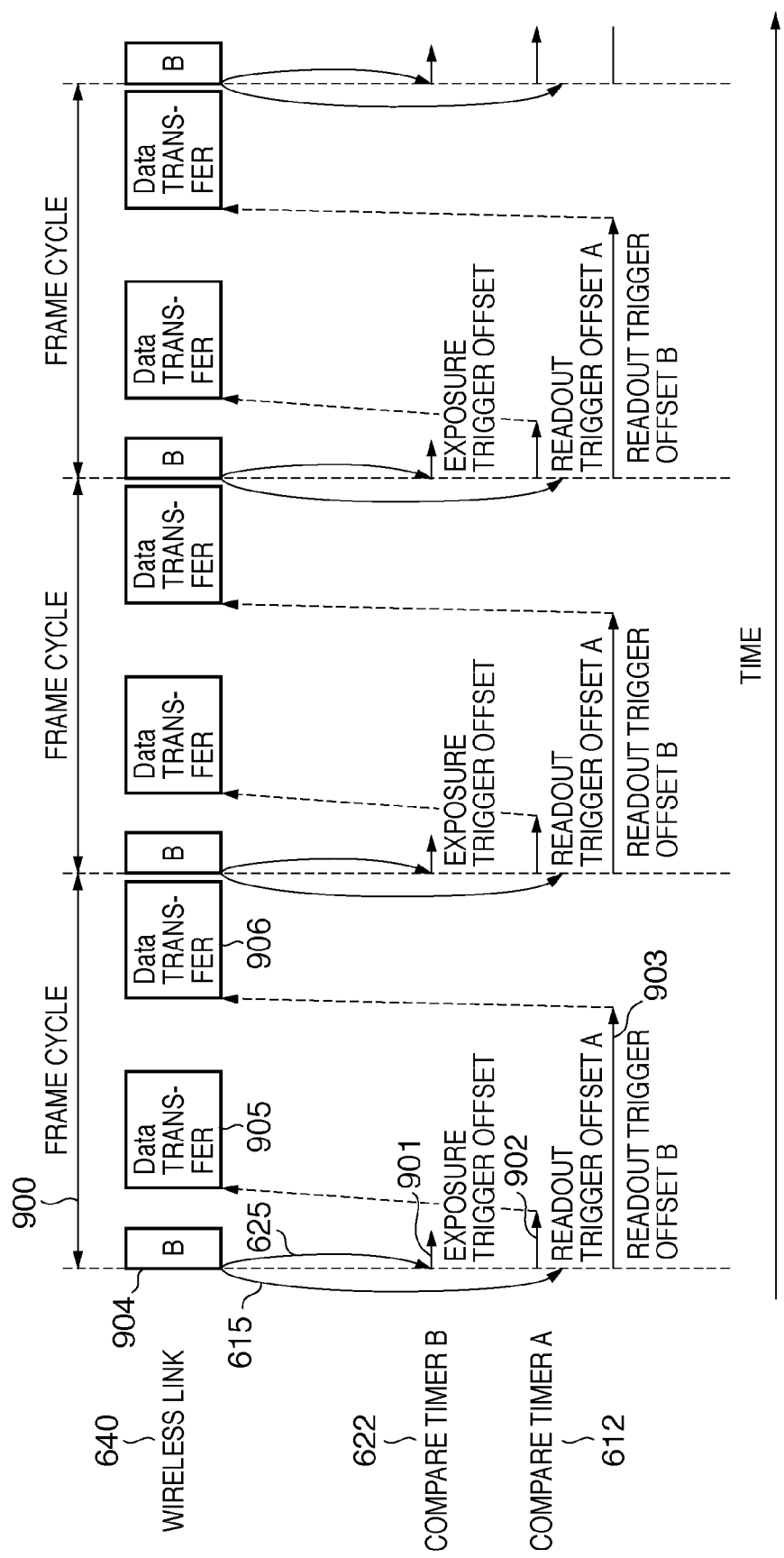
FIG. 9 is an example of a timing sequence diagram according to the first embodiment of the present invention.

FIG. 9 is an example of a timing sequence diagram. In fluoroscopic imaging, X-ray exposure is performed for each frame cycle 900, and field intensity distribution information obtained by the sensor unit 610 is read out. As described previously, it is necessary to strictly manage the X-ray exposure timing and sensor readout timing. This embodiment handles the case where readout must be performed twice for each frame, and the present invention is applicable to the case where readout must be performed once or more for each frame. This similarly applies to the following embodiments, and hence will not be repeated in these embodiments.

The frame cycle 900 is the imaging cycle of an X-ray image. The frame cycle 900 is 500 ms when the number of frames per sec is two, and about 33.3 ms when the number of frames per sec is thirty. An exposure trigger offset 901 is an offset from the start of a frame to the output of the exposure trigger signal from the compare timer B 622. A readout trigger offset A 902 is an offset from the start of a frame to the output of the first readout trigger signal from the compare timer A 612. A readout trigger offset B 903 is an offset from the start of a frame to the output of the second readout trigger signal from the compare timer A 612. A beacon signal (B) 904 is a beacon signal used by the wireless link 640. When the sensor unit 610 completes readout, the image data is transferred as indicated by 905 and 906 via the wireless link 640.

The operation of the whole X-ray fluoroscopic imaging system according to the present invention will be explained in detail below with reference to FIGS. 7 to 9 explained above. The CPUs 713 and 721 of the individual units perform this operation by executing computer programs loaded into the memories 714 and 722, respectively.

First, the following settings are performed prior to fluoroscopic imaging.

The frame cycle 900 is set in the timing generation unit 623 in the image processing unit 620. Also, a counter value corresponding to the exposure trigger offset 901 is set in the comparison register A 804 in the compare timer B 622. This counter value is the number of clocks generated by the oscillator 820 within a desired time. This similarly applies to the following counter values. That is, a counter value corresponding to the readout trigger offset A 902 is set in the comparison register A 804 in the compare timer A 612. Also, a counter value corresponding to the readout trigger offset B 903 is set in the comparison register B 805.

Furthermore, comparison registers except for those in which the counter values are set as described above are not used in this embodiment, and hence are cleared to "0" so as not to generate any extra one-shot pulse output.

Note that in this embodiment, the beacon counter 802 of each of the compare timers 612 and 622 necessarily outputs the counter reset signal 809 when receiving the compare timer reset signal 821. Note also that the trigger active register 803 of each of the compare timers 612 and 622 is set to "trigger output enable".

On the basis of the above-mentioned initial settings, the operations of the image processing unit 620 and sensor unit 610 after the start of a frame will be explained below.

First, the operation of the image processing unit 620 will be explained. The timing generation unit 623 sends the timing signal 624 to the wireless communication unit B 621 at a preset interval. As described previously, the frame cycle is preset at this interval. The wireless communication unit B 621 having received the timing signal 624 makes preparations for transmitting a beacon signal 904, and transmits the beacon signal 904 by the wireless link 640. At the same time, the wireless communication unit B 621 sends the compare timer B reset signal 625 to the compare timer B 622. The beacon counter 802 of the compare timer B 622 having received the compare timer B reset signal 625 outputs the counter reset signal 809.

The counter 801 of the compare timer B 622 having received the counter reset signal 809 is reset and starts counting from "0". Since the counter 801 counts up for each clock generated by the oscillator 820, each comparison register in the compare timer B 622 compares the counter value with the offset value set in the comparison register whenever count-up is performed. As described earlier, a counter value corresponding to the exposure trigger offset 901 is set in the comparison register A 804. Therefore, when the counter value of the counter 801 matches the counter value corresponding to the exposure trigger offset 901, the comparison register A 804 outputs a one-shot pulse output.

In response to the one-shot pulse output from the comparison register A 804, the OR gate 807 outputs a signal regardless of the outputs from other comparison registers. In addition, since the trigger active register 803 is set to "trigger output enable" in this embodiment, the compare timer B 622 outputs the exposure trigger signal 641 through the AND gate 808.

The output exposure trigger signal 641 is sent to the high voltage generation unit 731 of the X-ray generation unit 630 through a wired signal line, and the X-ray tube 631 emits radiation.

The operation of the sensor unit 610 will now be explained. The wireless communication unit A 611 having received the beacon signal 904 outputs the compare timer A reset signal 615 to the compare timer A 612 immediately after confirming that the received signal is the beacon signal 904. The beacon counter 802 of the compare timer A 612 having received the compare timer A reset signal 615 outputs the counter reset signal 809.

The counter 801 of the compare timer A 612 having received the counter reset signal 809 is reset and starts counting from "0". Since the counter 801 counts up for each clock generated by the oscillator 820, each comparison register in the compare timer A 612 compares the counter value with the offset value set in the comparison register whenever count-up is performed. As described earlier, a counter value corresponding to the readout trigger offset A 902 is set in the comparison register A 804. Also, a counter value corresponding to the readout trigger offset B 903 is set in the comparison register B 805. Therefore, when the counter value of the counter 801 matches the counter value corresponding to the readout trigger offset A 902, the comparison register A 804 outputs a one-shot pulse output.

In response to the one-shot pulse output from the comparison register A 804, the OR gate 807 outputs a signal regardless of the outputs from other comparison registers. In addition, since the trigger active register 803 is set to "trigger output enable" in this embodiment, the compare timer A 612 outputs the first readout trigger signal 716 to the front-end 712 through the AND gate 808. The front-end 712 having received the readout trigger signal 716 starts reading out data from the X-ray sensor 711. The readout data is, for example, an image obtained when X-rays are emitted.

In addition, when the counter value of the counter 801 having continued counting up matches the counter value corresponding to the readout trigger offset B 903, the comparison register B 805 outputs a one-shot pulse output. In the same manner as described above, the front-end 712 starts reading out data from the X-ray sensor 711. The readout data is, for example, an image obtained when no X-rays are emitted.

The above operation is repeated by beacon transmission synchronized with the frame cycle 900. This makes it possible to synchronize the timings of the compare timer A 612 in the sensor unit 610 and the compare timer B 622 in the image processing unit 620 for each frame cycle 900. Consequently, synchronization errors between the units 610 and 620 can be reduced.

Second Embodiment

In the first embodiment, the method of synchronizing the timings of the wirelessly connected sensor unit and image processing unit by using the beacon signal synchronized with the frame cycle has been described. In the second embodiment, an application form of the present invention when performing angiography or the like by which fluoroscopic imaging is performed while changing the frame cycle will be described.

To explain an outline of this embodiment, the case where the first frame cycle is changed to the second frame cycle will be explained. Assume that fluoroscopic imaging is performed by the first readout trigger offset and first exposure trigger offset for use in the first frame cycle. The second readout trigger output and second exposure trigger offset for use in the second frame cycle are saved in a sensor unit 610 and image processing unit 620 beforehand. The first frame cycle is switched to the second frame cycle in response to the transmission of a beacon signal.

Figure 10:
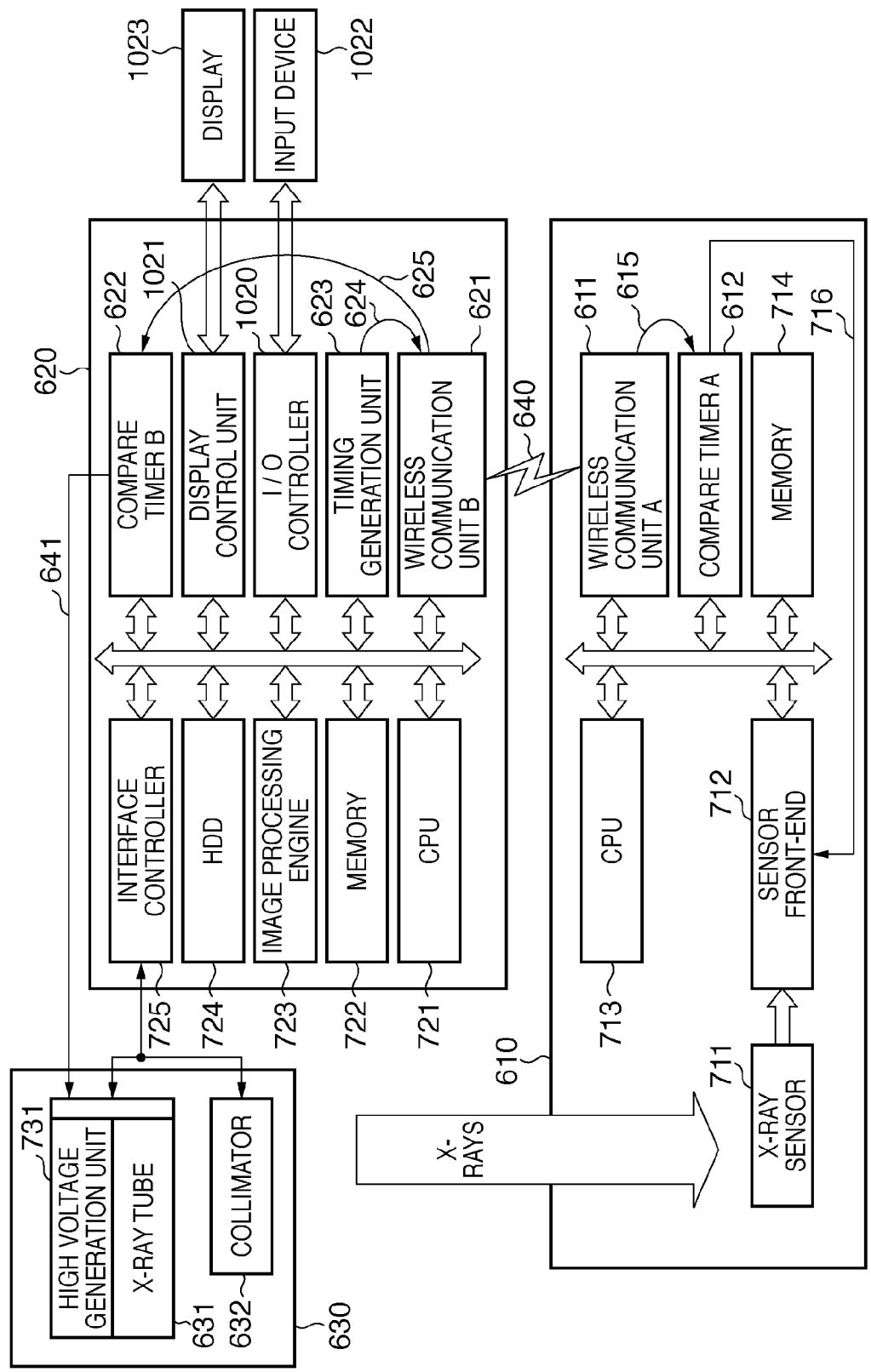
FIG. 10 is an example of a system block diagram according to the second embodiment of the present invention.

The arrangements of this embodiment will be explained below with reference to FIGS. 10 and 11. FIG. 10 is an example of a system block diagram according to the second embodiment of the present invention. The same reference numerals as in FIG. 7 explained in the first embodiment denote the same parts in FIG. 10, and a repetitive explanation will be omitted.

The image processing unit further includes an I/O controller 1020, display control unit 1021, input device 1022, and display 1023 in addition to the arrangement shown in FIG. 7. The I/O controller 1020 provides a user with a user interface for setting parameters and selecting operations. The display control unit 1021 generates a graphical user interface by which the user operates the fluoroscopic imaging system. The input device 1022 is, for example, a keyboard, touch panel, or mouse directly operated by the user. The display 1023 displays the graphical user interface.

Figure 11:
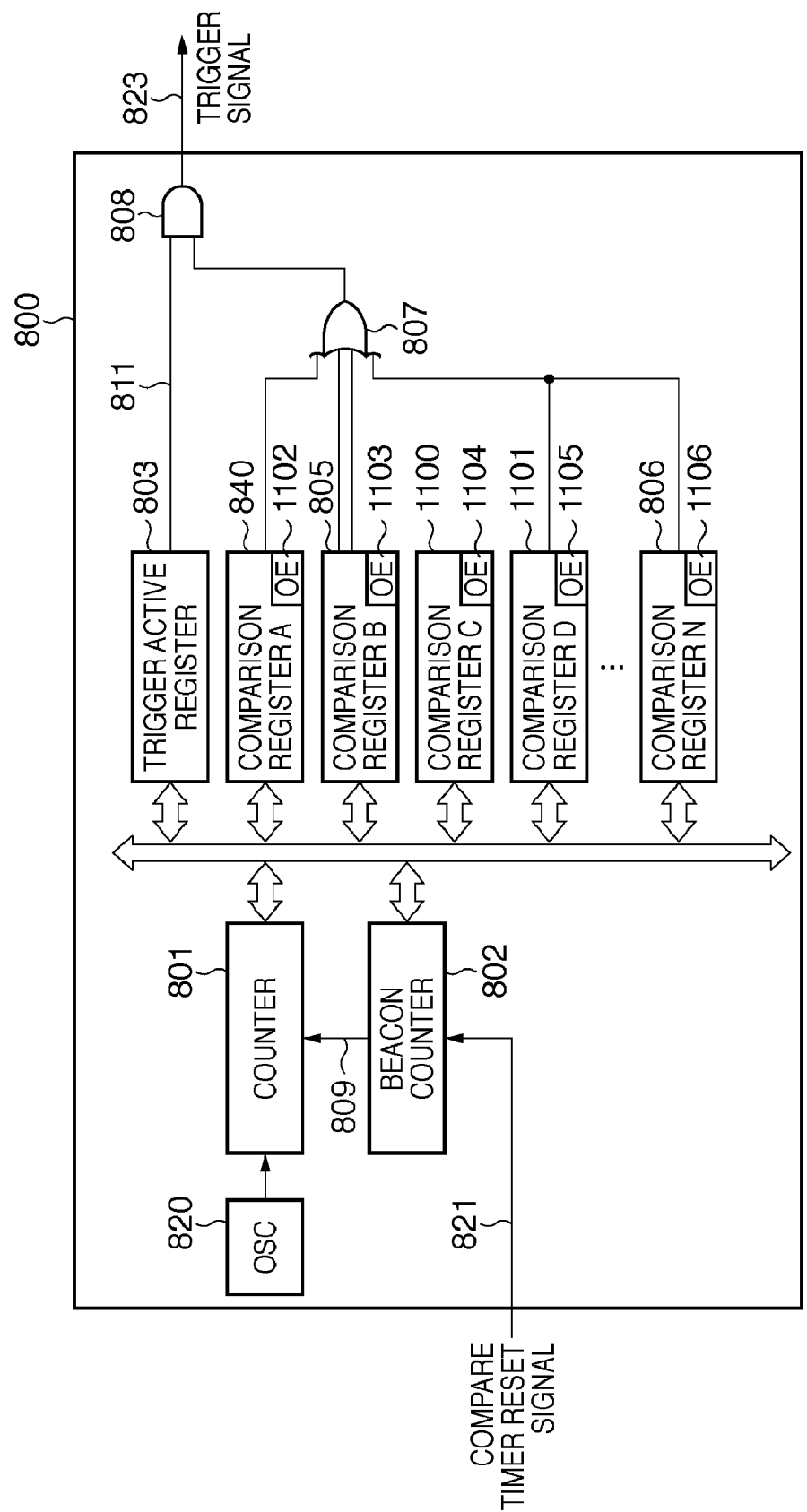
FIG. 11 is an example of an internal block diagram of a compare timer according to the second embodiment of the present invention.

FIG. 11 is an example of an internal block diagram of a compare timer according to the second embodiment of the present invention. The same reference numerals as in FIG. 8 explained in the first embodiment denote the same parts in FIG. 11, and a repetitive explanation will be omitted.

A compare timer 800 further includes a comparison register C 1100, a comparison register D 1101, and flags (OE) 1102 to 1106 in the comparison registers in addition to the constituent components shown in FIG. 8. The flags 1102 to 1106 control permission/prohibition of one-shot pulse outputs from the comparison registers. When the flag is set to "permit output", the one-shot pulse output can be output. When the flag is set to "prohibit output", no one-shot pulse output is output even if the counter value of the comparison register matches a predetermined counter value.

Figure 12:
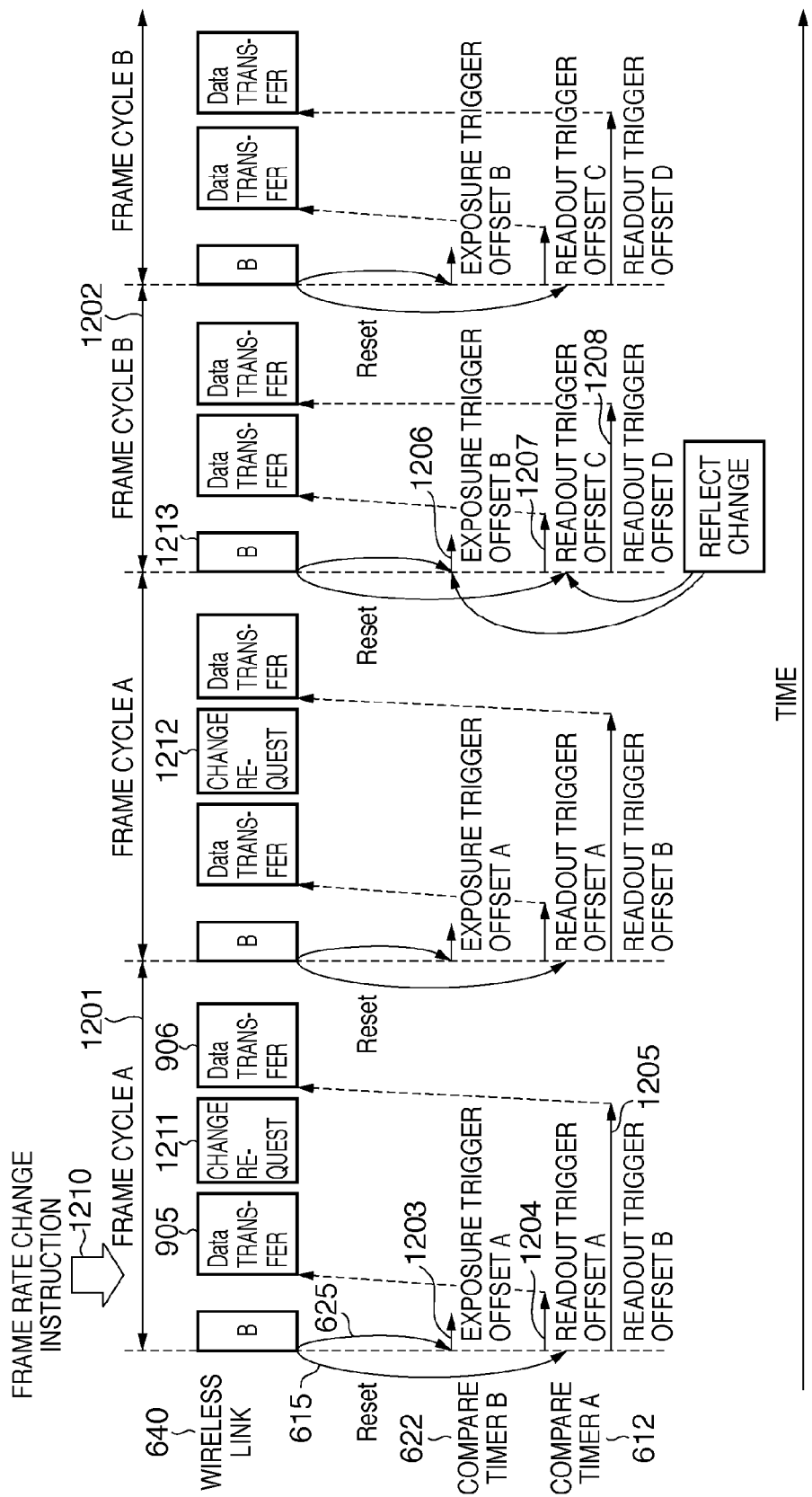
FIG. 12 is an example of a timing sequence diagram according to the second embodiment of the present invention.

The timing sequence of this embodiment will be explained below with reference to FIG. 12. FIG. 12 is an example of a timing sequence diagram according to the second embodiment of the present invention. The same reference numerals as in FIG. 9 explained in the first embodiment denote the same parts in FIG. 12, and a repetitive explanation will be omitted.

In fluoroscopic imaging of this embodiment, X-ray exposure is performed for each frame cycle a 1201, and field intensity distribution information obtained by the sensor unit 610 is read out. After that, the frame rate is switched midway to a frame cycle B 1202. The values of an exposure trigger offset and readout trigger offset are also changed to correspond to the changed frame cycle. Fluoroscopic imaging in the frame cycle a 1201 uses an exposure trigger offset A 1203, read out trigger offset A 1204, and read out trigger offset B 1205. Fluoroscopic imaging in the frame cycle B 1202 uses an exposure trigger offset B 1206, readout trigger offset C 1207, and readout trigger offset D 1208.

Processes performed by the image processing unit 620 and sensor unit 610 from the activation of an X-ray fluoroscopic imaging system according to the present invention to the change of the frame rate will be explained below with reference to FIGS. 13A to 13C. FIGS. 13A to 13C are an example of a frame rate switching flowchart according to the second embodiment of the present invention. CPUs 713 and 721 perform this flowchart by executing computer programs loaded into memories 714 and 722, respectively.

In step S1300, initialization is performed by activating the image processing unit 620. In step S1350, initialization is performed by activating the sensor unit 610.

After that, in step S1301, the image processing unit 620 sets "trigger output disable" in a trigger active register 803 of a compare timer B 622 in the image processing unit 620. In step S1351, the sensor unit 610 sets "trigger output disable" in a trigger active register 803 of a compare timer A 612 in the sensor unit 610. These settings inhibit outputting of a trigger signal 823 from each compare timer 800.

In step S1302, the image processing unit 620 initializes a wireless communication unit B 621. In step S1352, the sensor unit 610 initializes a wireless communication unit A 611. These processes establish a wireless link 640 using the wireless communication unit B 621 as an AP or PNC. Since it is unnecessary to define a beacon interval for use in the wireless link 640 at this timing, any cycle suitable for the wireless communication standards is used.

When the preparations up to this point are completed, the process advances to step S1303, and the image processing unit 620 displays the graphical user interface (GUI) on the display 1023 via the display control unit 1021, and accepts the selection of work contents from the user. While referring to the GUI, the user selects the procedure of desired work contents by operating the input device 1022.

In step S1304, whether the selection of the procedure is completed is determined. If the selection is not completed ("NO" in step S1304), the process returns to step S1303, and the procedure selection menu is kept displayed. If the selection is completed ("YES" in step S1304), the process advances to step S1304.

In step S1305, procedure information input from the input device 1022 is transmitted to the CPU 721 via the I/O controller 1020. The CPU 721 determines whether "fluoroscopic imaging" is selected as the procedure. If "fluoroscopic imaging" is selected ("YES" in step S1305), the process advances to step S1306. If "fluoroscopic imaging" is not selected ("NO" in step S1305), another procedure is performed. However, an explanation of the other procedure will be omitted.

In step S1306, the CPU 721 displays, on the display 1023, a GUI for prompting the user to set fluoroscopic imaging parameters such as a frame rate, tube current, and tube voltage to be applied to fluoroscopic imaging, and accepts inputting from the user.

As described in the first embodiment, a frame cycle determined from the frame rate set by the user is used as a beacon interval. The CPU 721 calculates a beacon interval from the set frame rate, and calculates counter values corresponding to an exposure trigger offset and readout trigger offset corresponding to the beacon interval. The image processing unit 620 sends, to the sensor unit 610, fluoroscopic parameters 1321 necessary for the sensor unit 610. The fluoroscopic imaging parameters 1321 include, for example, the parameters set by the user and the calculated counter value corresponding the readout trigger offset.

In step S1307, the image processing unit 620 sets the beacon interval in a timing generation unit 623. Accordingly, the beacon signal is sent at the beacon interval set in the timing generation unit 623.

Since the exposure trigger offset A 1203 is used in the frame cycle A 1201, the image processing unit 620 sets a counter value corresponding to this value in the comparison register A 804 of the compare timer B 622. In addition, the image processing unit 620 sets the flag 1102 of the comparison register A to "permit output". The image processing unit 620 sets the flags 1103 to 1106 of other comparison registers to "prohibit output".

There is a case in which a comparison register having an active flag outputs a one-shot pulse output. However, no X-ray exposure is started by mistake because the trigger active register 803 is set to "trigger output disable" in step S1301.

In step S1353, the sensor unit 610 sets, in the compare timer A 612, a counter value corresponding to the readout trigger offset contained in the received fluoroscopic parameters 1321. Since the readout trigger offset A 1204 and readout trigger offset B 1205 are used in the frame cycle A 1201, counter values corresponding to these values are set in the comparison registers A 804 and B 805 in the compare timer A 612. Furthermore, the flags 1102 and 1103 of the comparison registers are set to "permit output". The flags 1104 to 1106 of other comparison registers are set to "prohibit output".

There is a case in which a comparison register having an active flag outputs a one-shot pulse output. However, no readout is started by mistake because the trigger active register 803 is set to "trigger output disable" in step S1351.

Since the preparations for fluoroscopic imaging are thus completed, the image processing unit 620 accepts a fluoroscopic imaging start instruction from the user in step S1308.

In response to the fluoroscopic imaging start instruction from the user ("YES" in step S1308), the CPU 721 sets "trigger output enable" in the trigger active register 803 of the compare timer B 622 in step S1309. Simultaneously, the wireless communication unit B 621 sends a trigger activation request message 1322 to the sensor unit 610. In step S1354, the sensor unit 610 determines whether the trigger activation request message 1322 is received. If the message is received ("YES" in step S1354), the sensor unit 610 sets "trigger output enable" in the trigger active register 803 of the compare timer A 612 in step S1355.

After the processing described above, in step S1310, the counter 801 is reset whenever a beacon signal 1323 is transmitted, and an X-ray tube 631 emits X-rays after the elapse of the exposure trigger offset A 1203 as in the first embodiment. Also, in step S1356, the counter 801 is reset whenever the beacon signal 1323 is received, and data is read out after the elapse of the readout trigger offset A 1204 as in the first embodiment. Data is also read out after the elapse of the readout trigger offset B 1205. Consequently, fluoroscopic imaging is started in the frame cycle A 1201.

The case where a request for changing the frame rate is issued while fluoroscopic imaging is performed in the frame cycle A 1201 will be described below. In step S1311, whether a frame rate change instruction is received from the user is determined. If the instruction is received ("YES" in step S1311), the process advances to step S1312. Assume that a frame rate change instruction 1210 is received from the user while fluoroscopic imaging is performed in the frame cycle A 1201 as shown in FIG. 12.

In step S1312 of FIG. 13B, in response to the frame rate change instruction 1210, the CPU 721 calculates a frame cycle, exposure trigger offset, and readout trigger offset from the requested changed frame rate. In the frame cycle B 1202, the exposure trigger offset B 1206 and readout trigger offsets C 1207 and D 1208 are used.

The CPU 721 sets a counter value corresponding to the exposure trigger offset B 1206 in a comparison register B 805 of the compare timer B 622. The flag 1103 of the comparison register B 805 is kept set to "prohibit output". At this timing, a comparison register A 804 alone has a flag set to "permit output". Even after the comparison register B 805 is set, therefore, X-ray exposure corresponding to the frame cycle A 1201 is continued.

Also, the image processing unit 620 sends a frame rate change request message 1211 to the sensor unit 610 via a wireless link 640. The frame rate change request message 1211 contains counter values corresponding to the readout trigger offsets C 1207 and D 1208. As shown in FIG. 12, the frame rate change request message 1211 is sent, for example, between data transfer operations.

In step S1357 of FIG. 13B, the sensor unit 610 determines whether the frame rate change request message 1211 is received. If the message is received ("YES" in step S1357), the process advances to step S1358.

In step S1358, the CPU 713 sets the counter values corresponding to the readout trigger offsets C 1207 and D 1208 in the comparison registers C 1100 and D 1101, respectively, of the compare timer A 612. The corresponding flags 1104 and 1105 are kept set to "prohibit output". At this timing, the comparison registers A 804 and B 805 alone have flags set to "permit output". Even after this setting, therefore, sensor readout corresponding to the frame cycle A 1201 is continued.

If the operation of changing the compare timer A 612 is completed in step S1359, the sensor unit 610 sends a frame rate change confirmation message 1212 to the image processing unit 620. As shown in FIG. 12, the frame rate change confirmation message 1212 is sometimes communicated by a frame different from that of the frame rate change request message 1211.

In step S1313 of FIG. 13B, the image processing unit 620 determines whether the frame rate change confirmation message 1212 is received. If the message is received ("YES" in step S1313), the image processing unit 620 can determine that both the image processing unit 620 and sensor unit 610 can operate in the frame cycle B 1202. Accordingly, the image processing unit 620 advances to step S1314, and changes the timing signal generation interval of the timing generation unit 623 to the frame cycle B 1202. As a consequence, a beacon signal is transmitted in the frame cycle B 1202 from the next timing signal.

In step S1315, the image processing unit 620 determines whether a beacon signal 1213 is transmitted. If the signal is transmitted ("YES" in step S1315), the process advances to step S1316.

In step S1316, the image processing unit 620 sets the flags 1102 of the comparison registers A 804 and B 805 of the compare timer B 622 to "prohibit output" and "permit output", respectively, immediately after transmitting the beacon signal 1213. By the above processing, X-ray exposure is performed in the frame cycle B 1202 after the transmission of the beacon signal 1213.

On the other hand, in step S1360, the sensor unit 610 determines whether the beacon signal 1213 is received. If the signal is received ("YES" in step S1360), the process advances to step S1361.

In step S1361, the sensor unit 610 sets the flags of the comparison registers A 804 and B 805 of the compare timer A 612 to "prohibit output" immediately after receiving the beacon signal 1213. Also, the sensor unit 610 sets the flags of the comparison registers C 1100 and D 1101 to "permit output". By the above processing, data is read out from the sensor in the frame cycle B 1202 after the reception of the beacon signal 1213.

The flags are changed within a time period much shorter than the exposure trigger offset and readout trigger offset. Since the beacon signal 1213 is transmitted, therefore, both the units can start processing by the trigger offset corresponding to the frame cycle B 1202. Note that as described previously, before the beacon signal 1213 is transmitted, fluoroscopic imaging is continued by the trigger offset corresponding to the frame cycle A 1201 even when the offset value corresponding to the frame cycle B 1202 is registered in the comparison registers. Accordingly, the offset value may also be registered in the comparison registers in the image processing unit 620 and those in the sensor unit 610 in different frames.

In this embodiment, the frame rate change performed by the frame rate change instruction 1210 from the user has been described. However, the frame rate change may also be preprogrammed and automatically requested.

The process advances to step S1319 if termination of fluoroscopic imaging is requested in step S1318 or if still image imaging after fluoroscopic imaging is requested in step S1317.

In step S1319, the CPU 721 of the image processing unit 620 sets "trigger output disable" in the trigger active register 803 of the compare timer B 622. In addition, the wireless communication unit B 621 sends a fluoroscopic imaging termination message 1327 to the sensor unit 610 to disable the trigger output.

In step S1362, the sensor unit 610 determines whether the fluoroscopic imaging termination message 1327 is received. If the message is received ("YES" in step S1362), the sensor unit 610 sets "trigger output disable" in the trigger active register 803 of the compare timer A 612 in step S1363.

In this embodiment as described above, even when performing fluoroscopic imaging while changing the frame rate, it is possible to synchronize the timings of the two compare timers for each beacon output, and reduce synchronization errors between the units 610 and 620. It is also possible to continuously change the frame cycle without stopping the system.

Third Embodiment

In each of the previous embodiments, the method of simply and accurately synchronizing the timings of the wirelessly connected sensor unit and image processing unit by using the beacon signal synchronized with the frame cycle has been described. In the third embodiment, a method of synchronizing the frame rate and beacon interval will be described.

Figure 1:
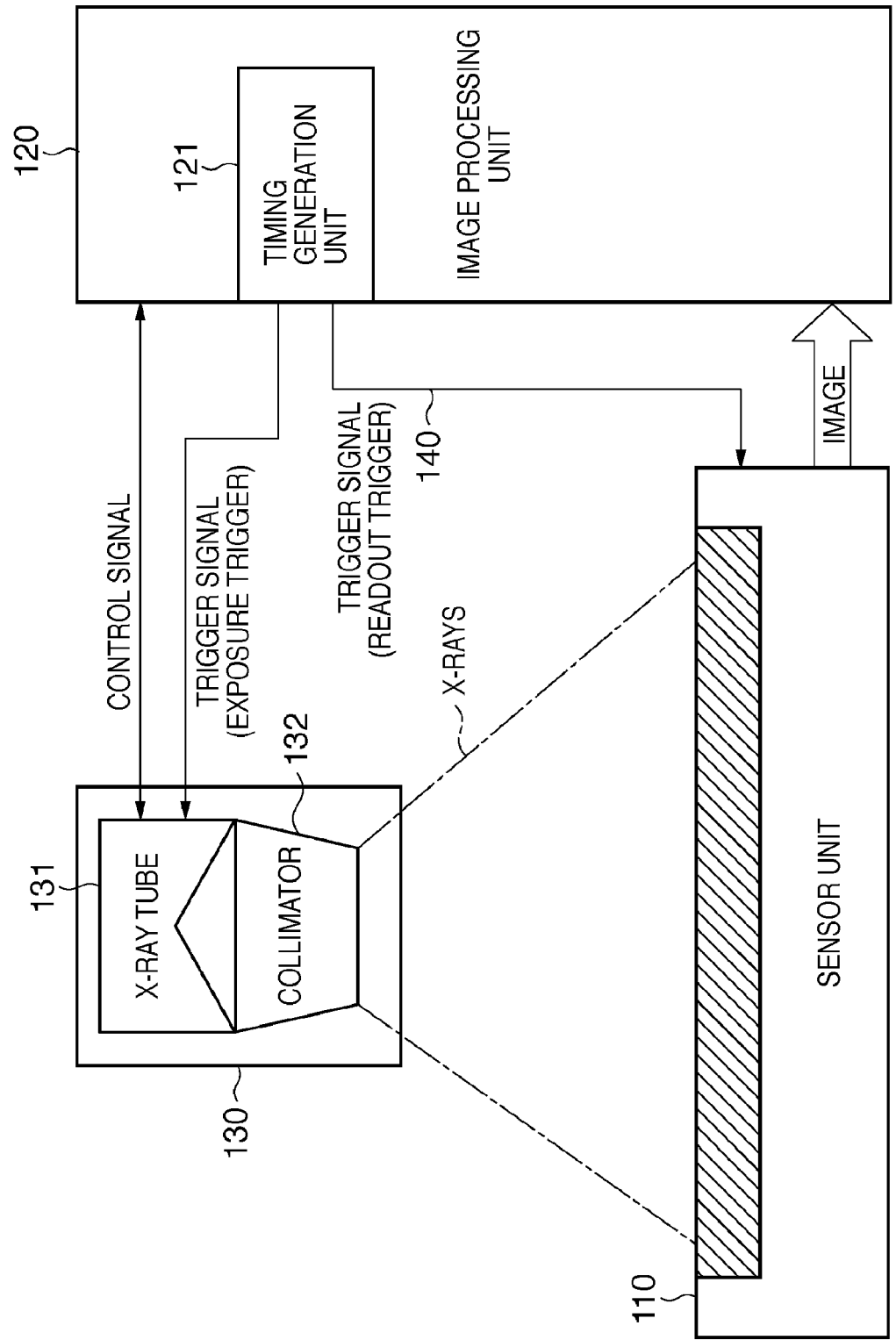
FIG. 1 is a view for explaining an example of an X-ray imaging system in which a sensor unit is separated.
Figure 2:
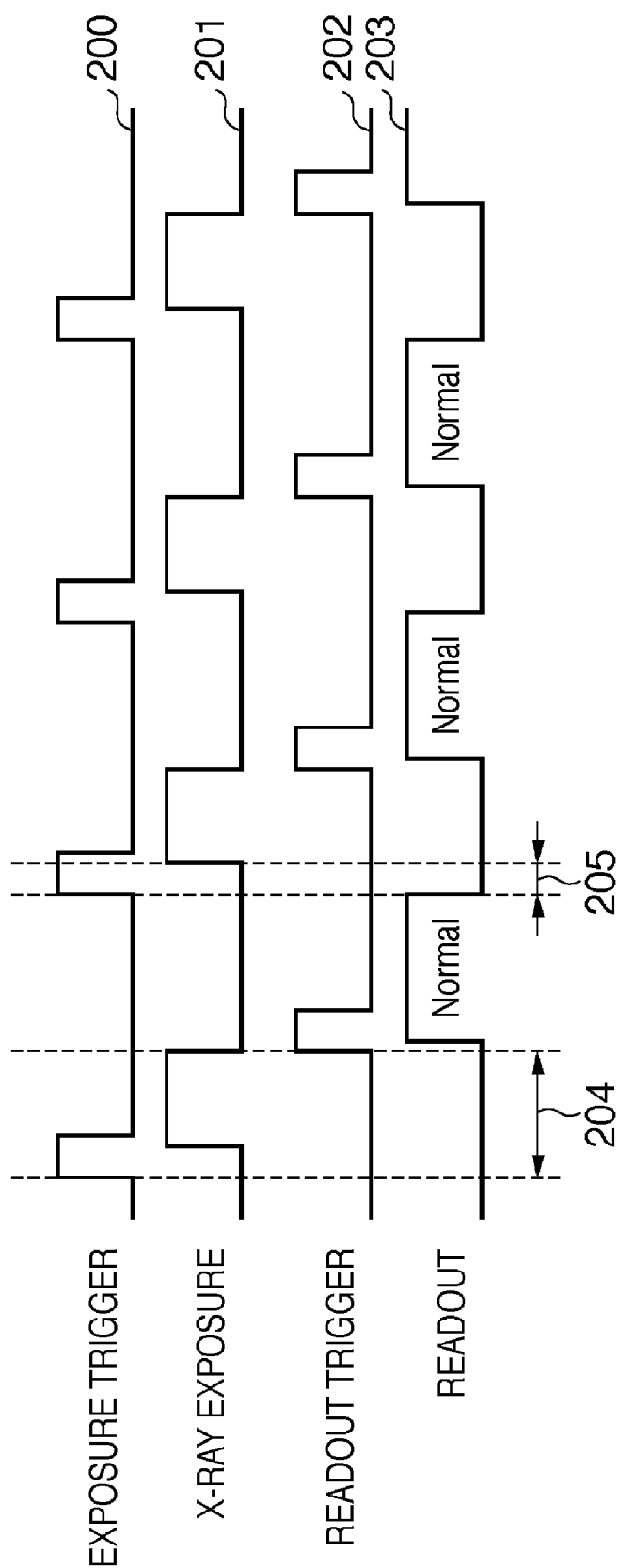
FIG. 2 is an example of a timing chart of exposure and readout when using a CMOS sensor.
Figure 3:
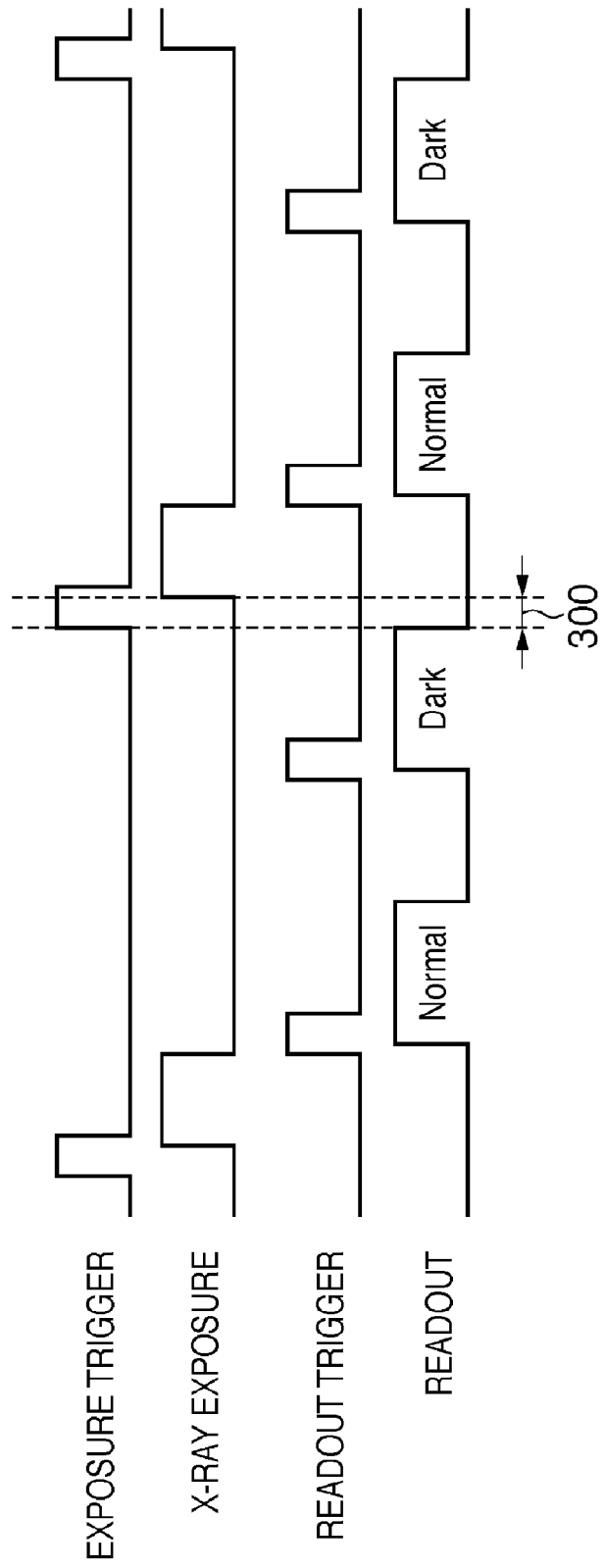
FIG. 3 is an example of a timing chart of exposure and readout when using a LANMIT sensor.
Figure 4:
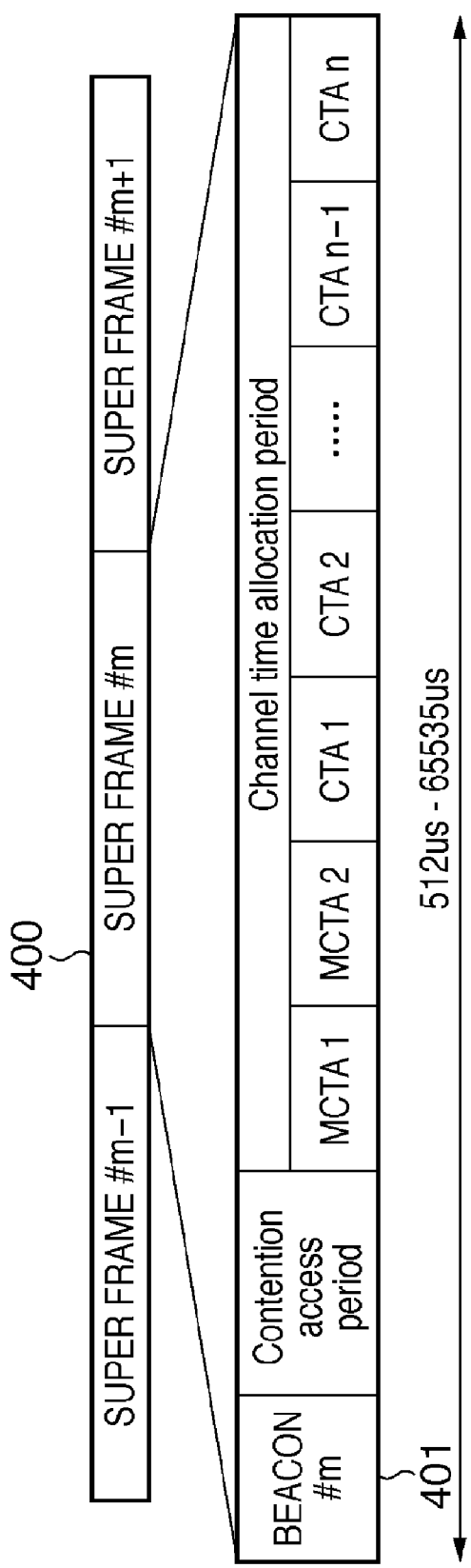
FIG. 4 shows an example of a super frame format complying with the IEEE802.15.3 standards.
Figure 5:
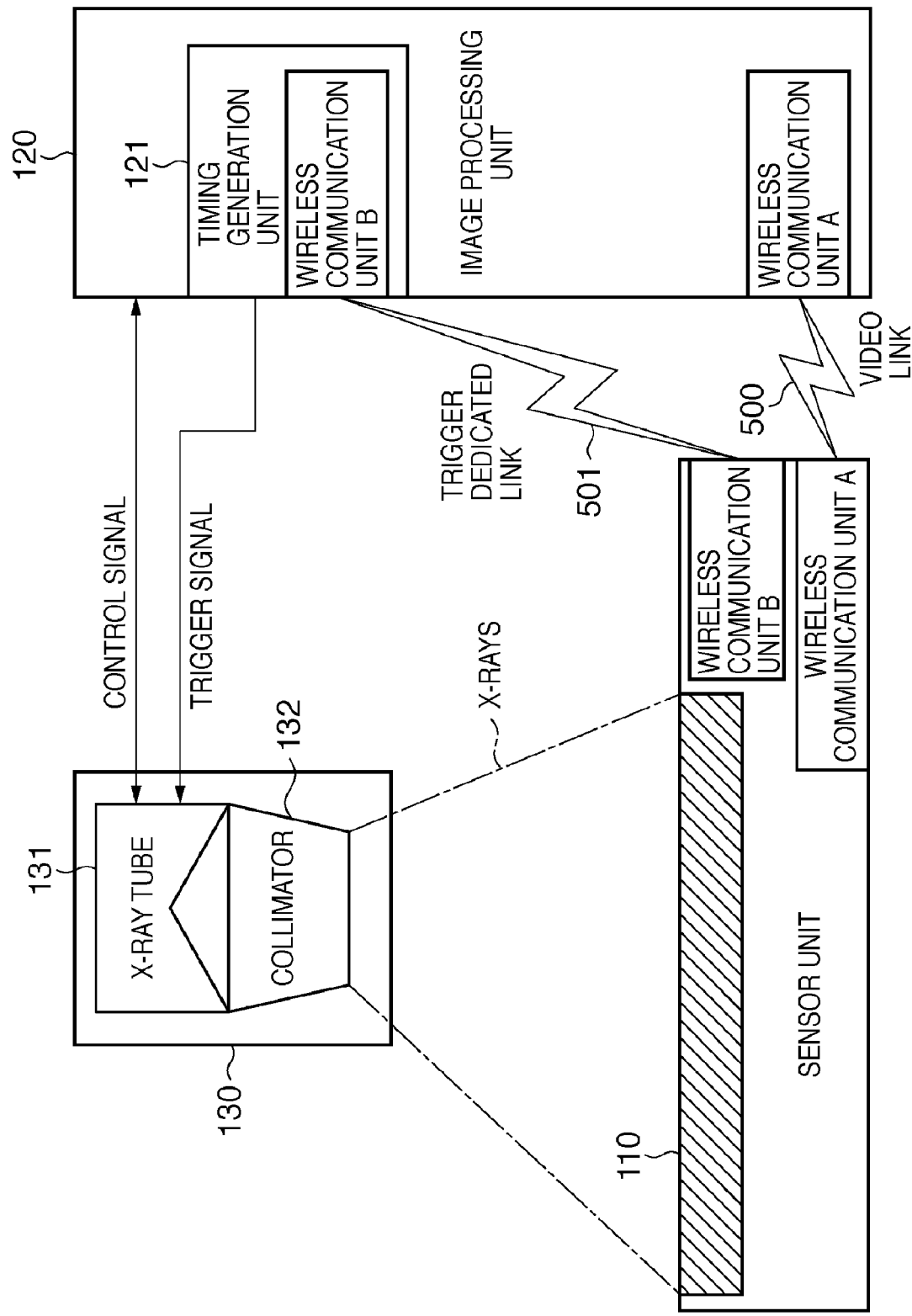
FIG. 5 shows an example of the system configuration of a wireless X-ray imaging system.

Generally speaking, when matching the frame cycle with the beacon interval, it is sometimes impossible to freely select the beacon interval unless unique wireless communication standards are defined. As shown in FIG. 4, for example, the beacon interval of the IEEE802.15.3 (UWB) standards can be selected from only 512 to 65,535 μsec. When represented by the frame rate, this range is 1,953 fps (=1/512 μsec) to 15.26 fps (=1/65,535 μsec). Actual fluoroscopic imaging is generally performed at a frame rate of about 0.1 to 200 fps. Accordingly, the above frame rate cannot be applied to fluoroscopic imaging performed at a frame rate lower than 15.26 fps. As described above, if the frame cycle and beacon interval cannot be matched, the aforesaid embodiments cannot be applied in their direct forms. In the third embodiment, therefore, a method of coping with a case like this will be explained.

The system configuration of the third embodiment is the same as that shown in FIG. 10. Also, the block diagram of a compare timer in this system configuration is the same as FIG. 11.

To adjust the beacon interval and frame cycle meeting the above-mentioned standard values, this embodiment particularly uses a beacon counter 802 in a compare timer 800. The beacon counter 802 counts a compare timer reset signal 821, and resets a counter 801 by a counter reset signal 809 only when receiving a predetermined number of signals.

FIG. 14 is a timing sequence diagram when performing fluoroscopic imaging at 10 fps by using the IEEE802.15.3 standards. FIG. 14 is an example of a timing sequence diagram according to the third embodiment of the present invention. As described above, the longest beacon interval settable by the IEEE802.15.3 standards is 65.535 ms. Since a frame cycle 1400 when performing fluoroscopic imaging at 10 fps is 100 ms, this frame cycle cannot be matched with the beacon interval unlike the above embodiment. Therefore, a beacon interval 1405 is set at 33.33 ms, and "3" as a natural number obtained by dividing the frame cycle by the beacon interval is set as a count in the beacon counter 802 in the compare timer 800. Consequently, the counter reset signal 809 is output only once when the compare timer reset signal 821 is detected three times. As described previously, the compare timer reset signal 821 is output whenever the beacon signal is transmitted. Therefore, counters 801 of compare timers A 612 and B 622 are reset only once whenever the beacon signal is transmitted three times. Accordingly, the counters 801 are reset to start counting from "0" for every 33.33 ms×3=100 ms.

Assume that the counter reset signal 809 is output when a beacon signal 1401 is transmitted. A frame is started when the counter reset signal 809 is received. In response to a beacon signal 1402 transmitted next, the compare timer reset signal 821 is output to the beacon counter 802. However, the beacon counter 802 has not reached a predetermined count yet, and hence does not output the counter reset signal 809. Accordingly, the frame is continued. This similarly applies to the case where a beacon signal 1403 is transmitted. When a beacon signal 1404 is transmitted, the beacon counter 802 outputs the counter reset signal 809, thereby starting a new frame.

Figure 15A:
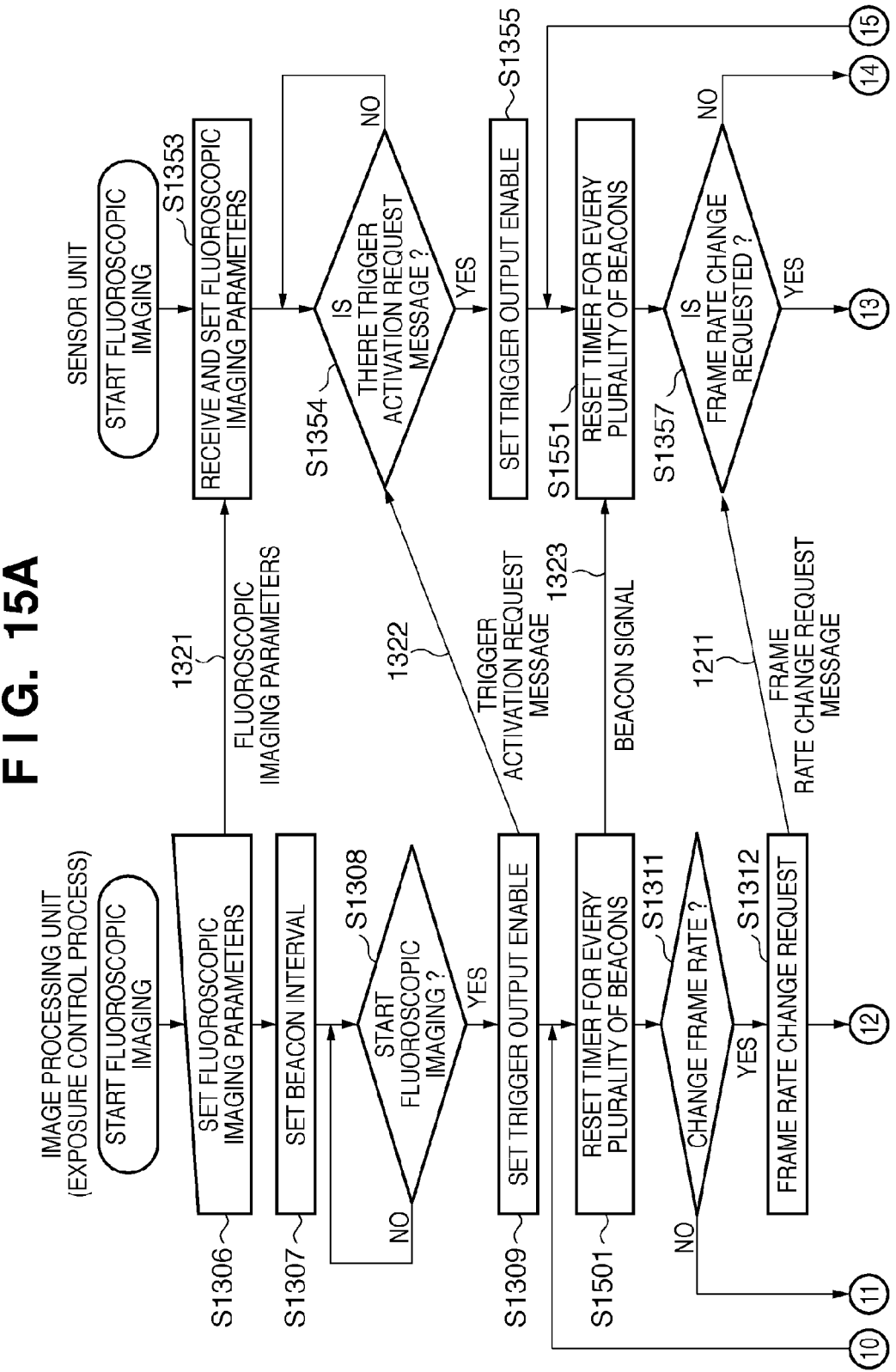
FIGS. 15A to 15C are flowcharts for explaining an example of the process of switching frame rates according to the third embodiment of the present invention.
Figure 15B:
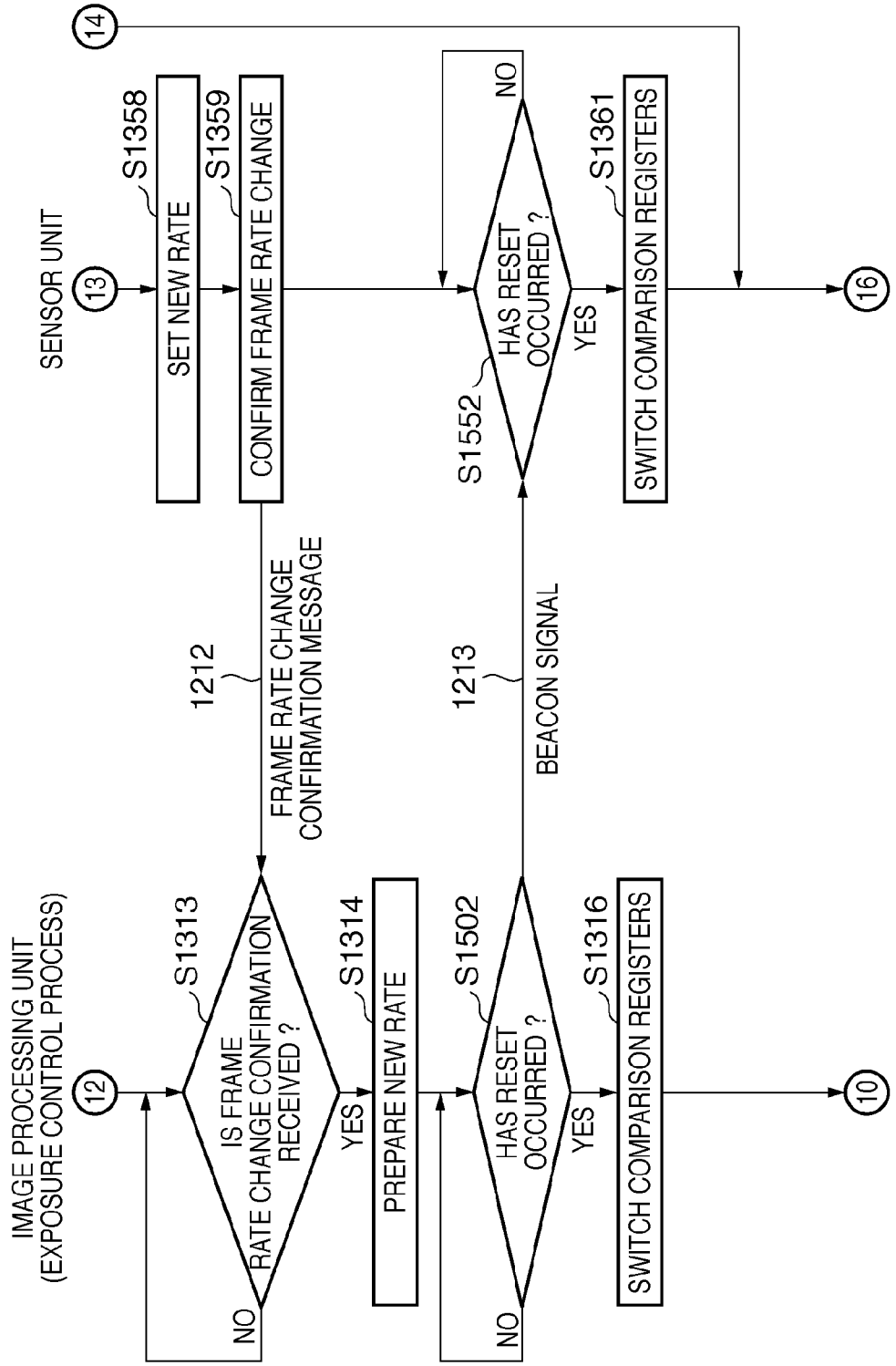
Figure 15C:
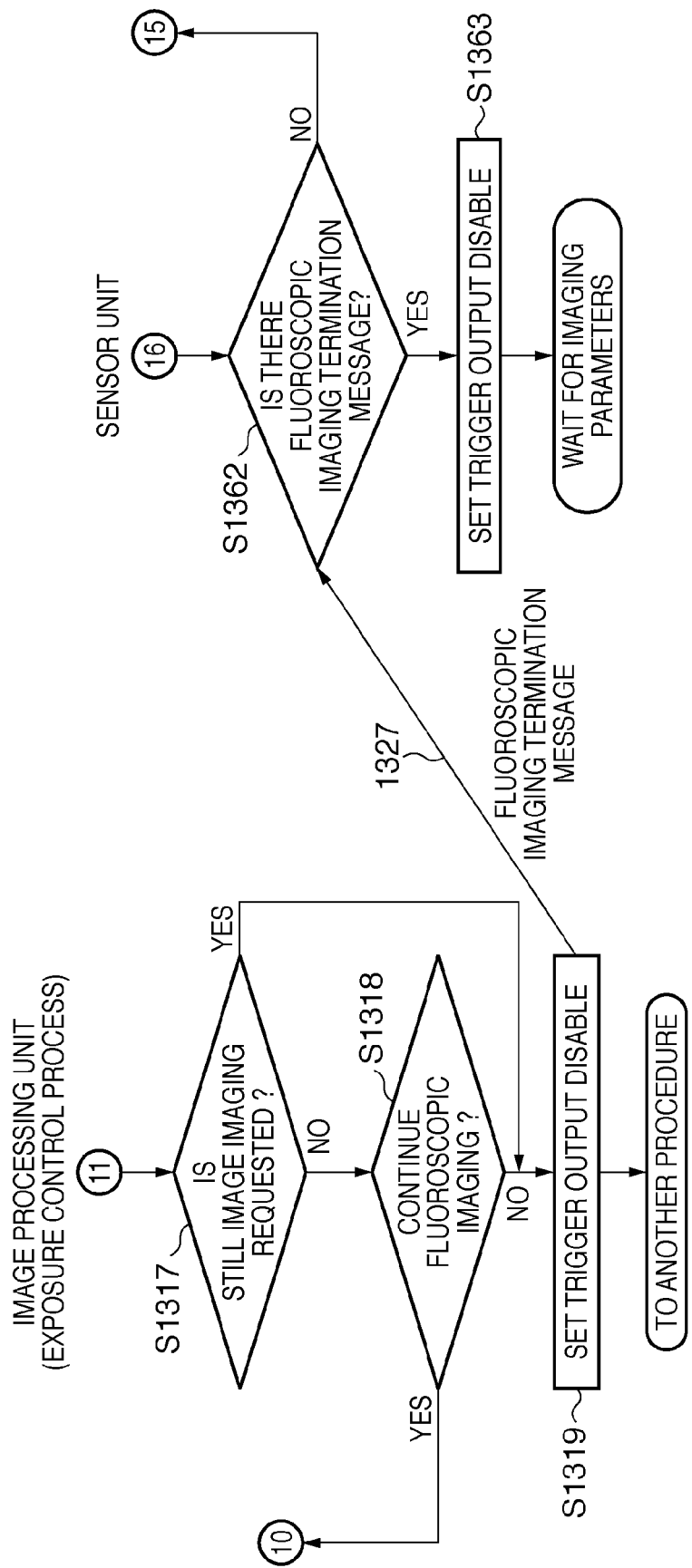

The process of resetting the counter 801 of the compare timer 800 when the beacon is generated a predetermined number of times will be explained below with reference to FIGS. 15A to 15C. FIGS. 15A to 15C are an example of a frame rate switching flowchart according to the third embodiment of the present invention. An explanation of the same processes as in FIGS. 13A to 13C will not be repeated, and only different processes will be explained below by denoting them by reference numerals shown in FIGS. 15A to 15C.

In steps S1501 and S1551 as described previously, the counters 801 of the compare timers 800 of the two units are reset whenever the beacon signal is received a predetermined number of times.

In steps S1502 and S1552, whether the counters 801 are reset is determined, and the counter value is changed to a set value corresponding to the changed frame cycle. This is so because if the timing of the frame cycle change is determined on the basis of the reception of the beacon signal, the set value may be changed even in the course of the frame.

In this embodiment as described above, even when using wireless communication standards by which the beacon interval cannot be prolonged, it is possible to synchronize the timings of the two compare timers for each frame, and reduce synchronization errors between units 610 and 620.

Fourth Embodiment

In the third embodiment, the method of applying the present invention to the case where the frame cycle is set to a time longer than the beacon interval defined by wireless communication standards has been described. In the fourth embodiment, the case where the frame cycle is set to a time shorter than the beacon interval will be described.

The beacon interval of the IEEE802.11 (wireless LAN) standards can be selected from 1 ms to a few ten ms on the ms order. However, when the beacon interval is shortened in any wireless communication standards, the beacon transmission time in communication increases, and this shortens a period usable for actual data communication. This poses the problem that the penalty for the transmission speed increases although the synchronization accuracy increases.

To solve this problem, a method of performing exposure a plurality of number of times during one beacon interval will be explained in this embodiment. The system configuration of the fourth embodiment is the same as that shown in FIG. 10. Also, the block diagram of a compare timer 800 in this system configuration is the same as FIG. 11.

Figure 16:
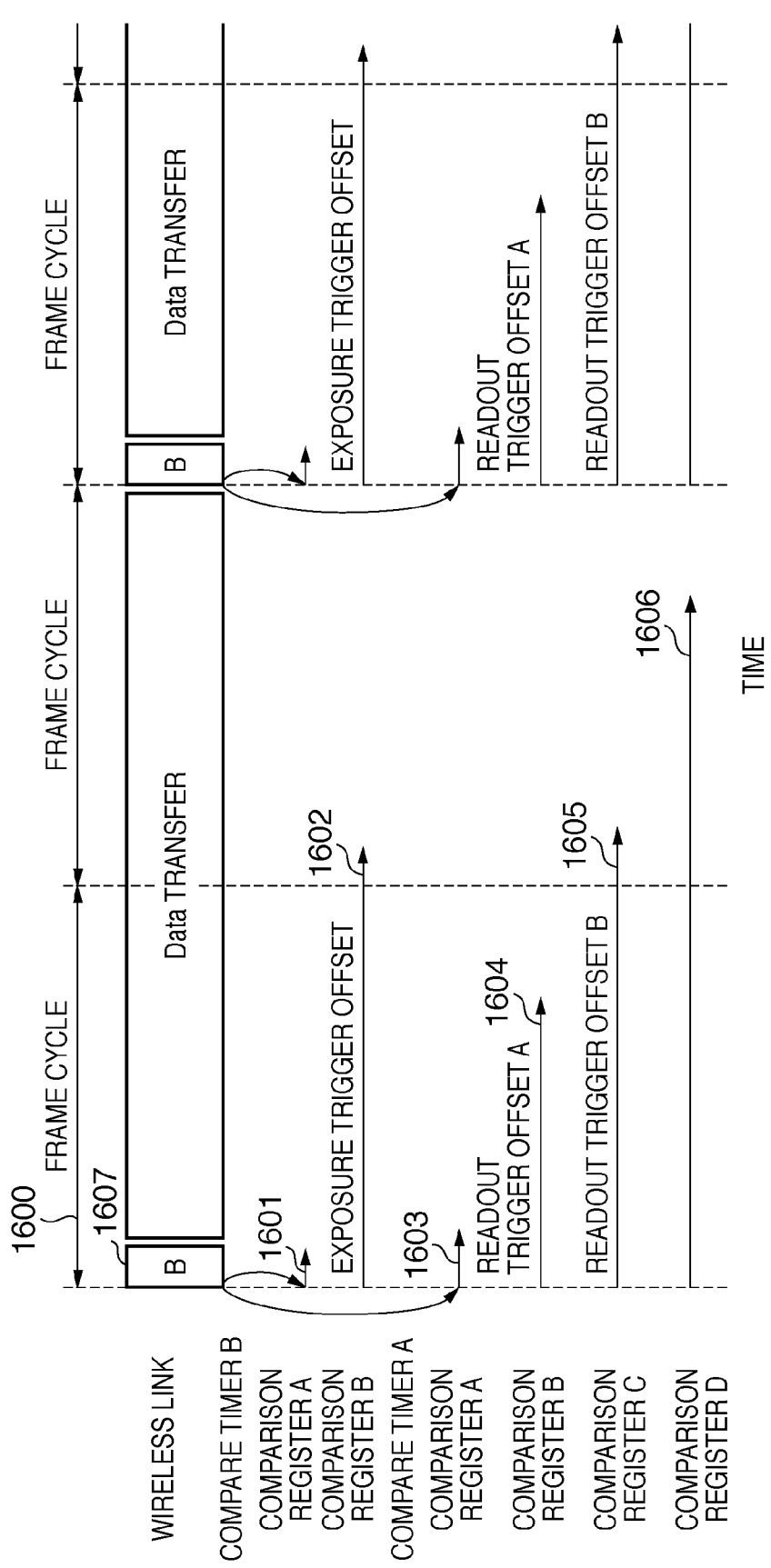
FIG. 16 is an example of a timing sequence diagram according to the fourth embodiment of the present invention.

A timing sequence diagram when performing exposure a plurality of number of times during one beacon interval will be explained below with reference to FIG. 16. FIG. 16 is an example of the timing sequence diagram according to the fourth embodiment of the present invention. In this embodiment, fluoroscopic imaging by which exposure is performed twice while one beacon signal is generated will be explained. However, the present invention is similarly applicable to the case where exposure is performed twice or more.

To perform exposure a plurality of number of times during one beacon interval as described above, the compare timer 800 of the present invention includes a plurality of comparison registers. A counter value corresponding to an exposure trigger offset 1601 is set in a comparison register A 804 of a compare timer B 622. Also, a counter value corresponding to a value 1602 obtained by adding a frame cycle 1600 to the exposure trigger offset 1601 is set in a comparison register B 805. To make one beacon interval contain three frames or more, a value obtained by multiplying the frame cycle 1600 by a natural number is added to the exposure trigger offset 1601.

Likewise, counter values corresponding to readout trigger offsets A 1603 and B 1604 are respectively set in comparison registers A 804 and B 805 of a compare timer A 612. A counter value corresponding to a value obtained by adding the frame cycle 1600 to the readout trigger offset A 1603 is set in a comparison register C 1100. Furthermore, a counter value corresponding to a value obtained by adding the frame cycle 1600 to the readout trigger offset B 1604 is set in a comparison register D 1101.

The above settings make it possible to execute two frames synchronized with a single beacon signal.

Also, a frame rate changing process of this embodiment is the same as that explained in the second embodiment. When using this embodiment, therefore, the frame rate is changed when fluoroscopic imaging of a plurality of frames synchronized with one beacon interval is completed. As a consequence, a time loss before the frame rate change is produced. However, this time loss is not a big problem because the beacon interval applied to the case described in this embodiment is normally 1 sec or less.

As described above, in this embodiment, the present invention can increase the time usable for data transfer while synchronizing an image processing unit 620 with a sensor unit 610 for each beacon.

Fifth Embodiment

In each of the previous embodiments, the method of synchronizing the timings of the sensor unit and image processing unit for each beacon signal by matching the beacon signal with the frame rate between the two units in the wireless X-ray fluoroscopic imaging system has been described. However, an AP or PNC is sometimes unable to transmit a beacon signal at a predetermined beacon interval because, for example, a large amount of data is communicated when transmitting the beacon.

In this case, synchronization is possible for each frame, but jitter occurs in each frame because a predetermined frame rate cannot be secured. To solve this problem, it is possible to use the IEEE802.15.3 standards capable of time management by using the TDMA scheme. However, it is sometimes necessary to use wireless communication standards using best effort type arbitration performed by the CSMA/CA scheme such as IEEE802.11. In the fifth embodiment, a method of ensuring an accurate frame rate while applying the present invention to best effort type wireless communication such as the CSMA/CA scheme will be explained.

Figure 18:
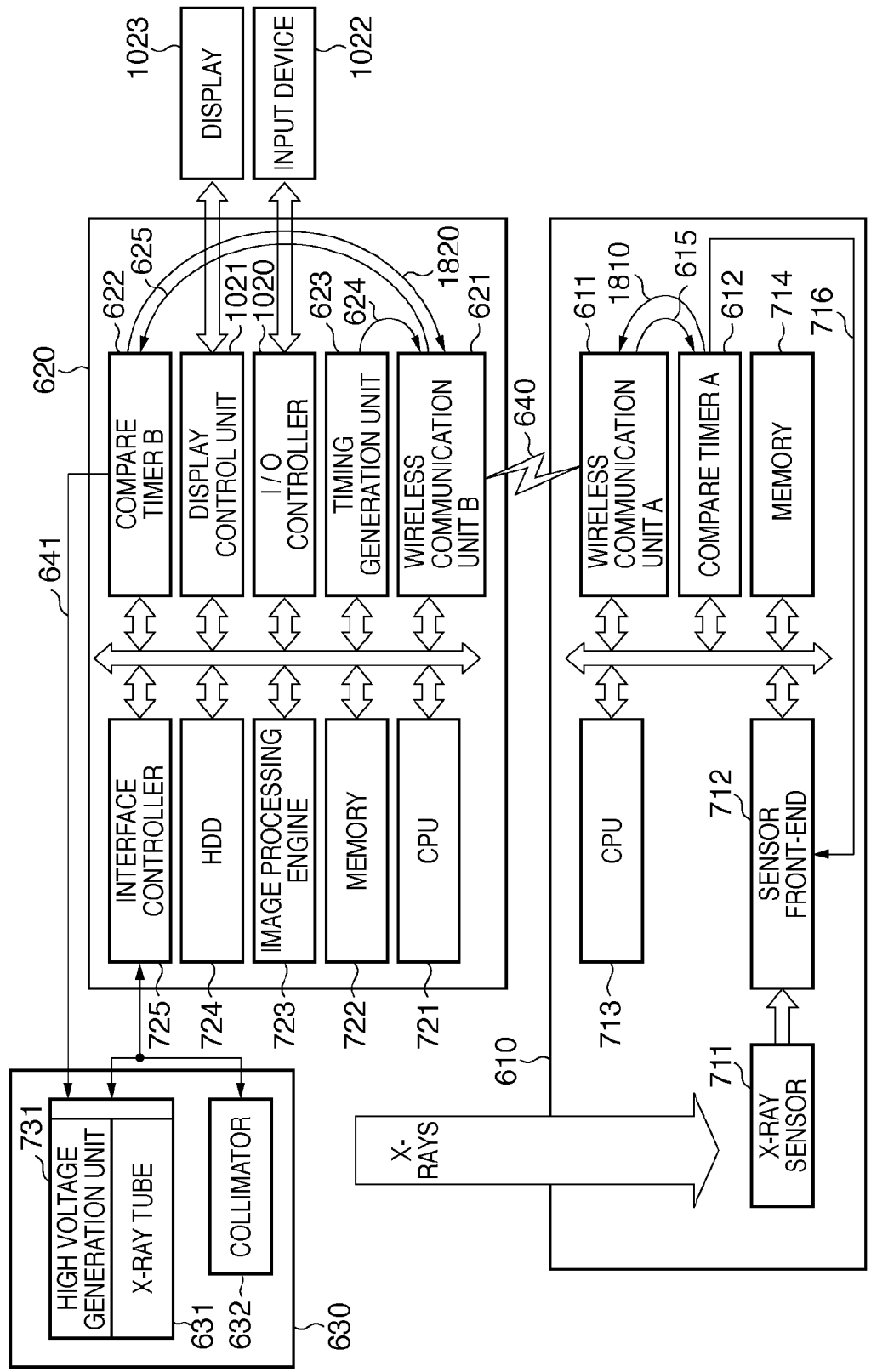
FIG. 18 is an example of a system block diagram according to the fifth embodiment of the present invention.

The arrangement of this embodiment will be explained below with reference to FIG. 18. FIG. 18 is an example of a system block diagram according to the fifth embodiment of the present invention. The same reference numerals as in FIG. 10 denote the same parts in FIG. 18, and a repetitive explanation will be omitted.

A compare timer B 622 sends a transfer interruption request signal B 1820 for requesting interruption of data transfer to a wireless communication unit B 621. This interrupts data transfer. Also, a compare timer A 612 sends a transfer interruption request signal A 1810 for requesting interruption of data transfer to a wireless communication unit A 611.

Figure 19:
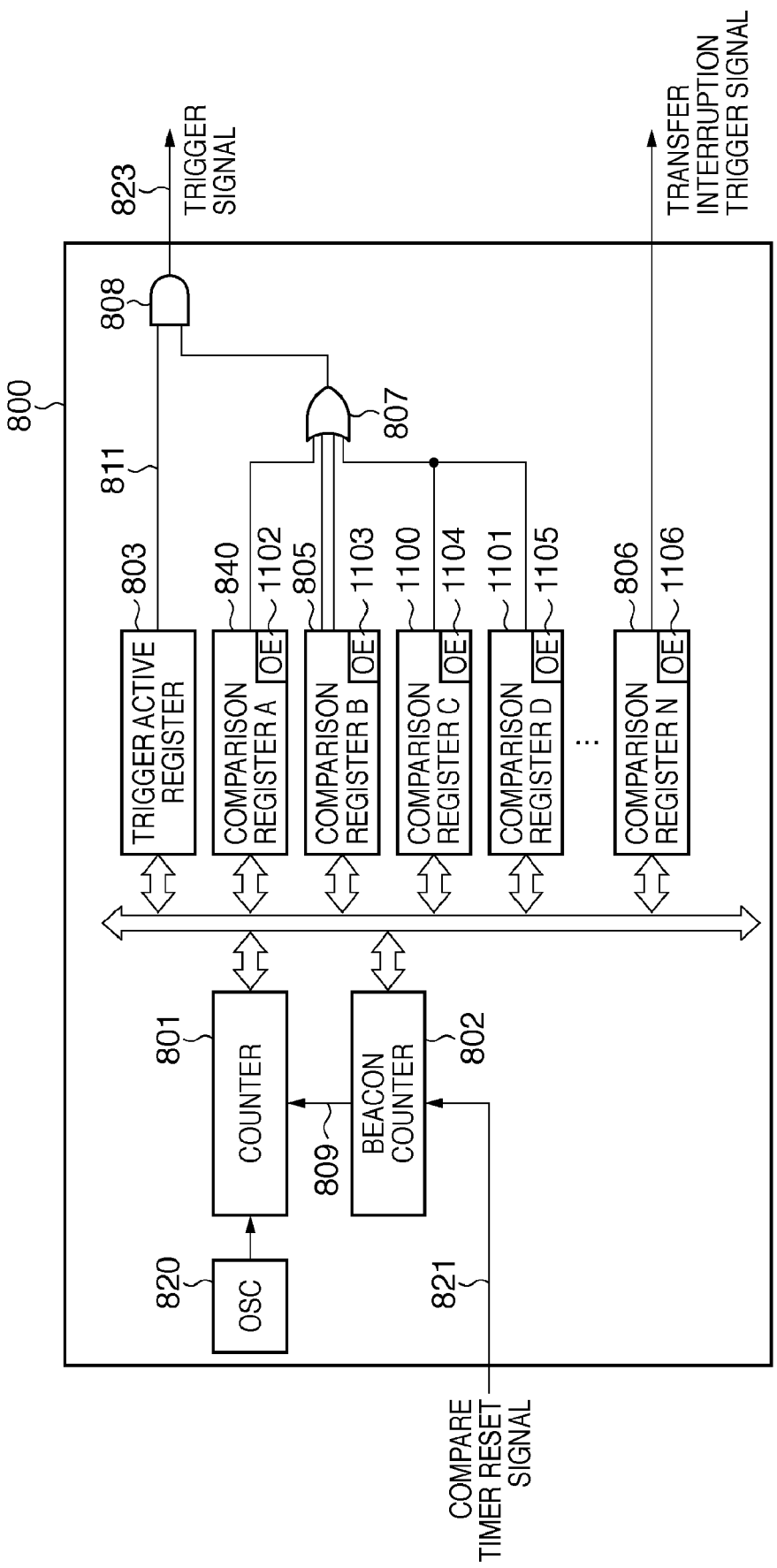
FIG. 19 is an example of an internal block diagram of a compare timer according to the fifth embodiment of the present invention.

FIG. 19 shows the internal configuration of a compare timer 800 according to this embodiment. The same reference numerals as in FIG. 11 denote the same parts in FIG. 19, and a repetitive explanation will be omitted. A comparison register N 806 outputs a transfer interruption trigger signal 1900 as a one-shot pulse output.

Figure 17:
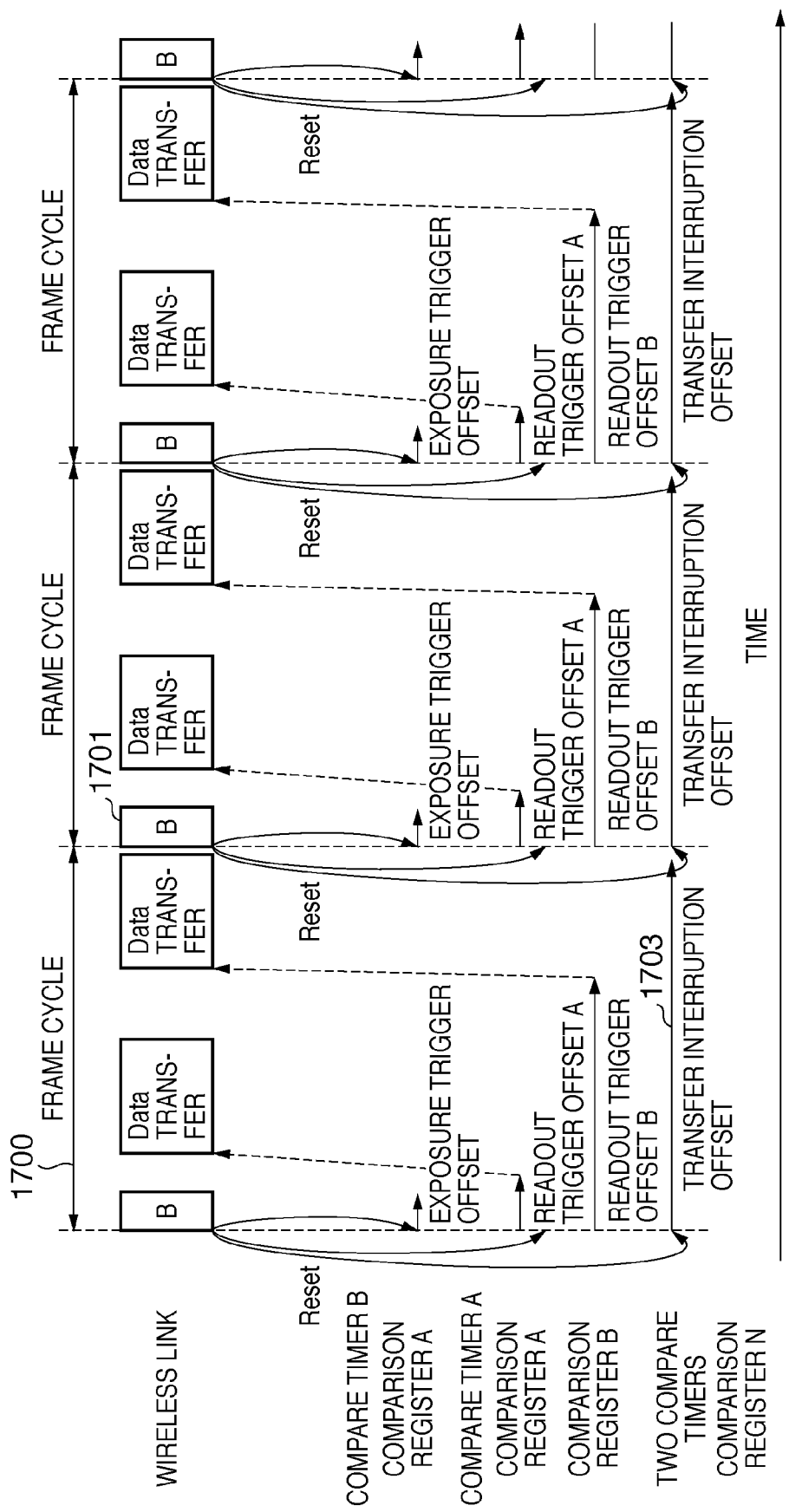
FIG. 17 is an example of a timing sequence diagram according to the sixth embodiment of the present invention.

A timing sequence diagram according to this embodiment will be explained below with reference to FIG. 17. FIG. 17 is an example of the timing sequence diagram according to this embodiment. The timing sequence is similar to that of the first embodiment explained with reference to FIG. 9, so differences will mainly be explained.

In fluoroscopic imaging of this embodiment, as in the first embodiment, a counter 801 of the compare timer 800 is reset for each beacon signal matching a frame cycle 1700, and the timings of X-ray exposure and readout are controlled on the basis of the offset time from the reset timing.

A counter value corresponding to a transfer interruption offset 1703 is set in the comparison registers N 806 in the two compare timers 800. The transfer interruption offset 1703 has a value obtained by subtracting, from the frame cycle 1700, a time necessary and sufficient to interrupt wireless communication being performed by the wireless communication units B 621 and A 611. By performing this setting, the wireless communication units 611 and 612 receive the transfer interruption trigger signal 1900 from the compare timer 800 immediately before a next beacon signal 1701 is transmitted. The wireless communication unit having received the transfer interruption trigger signal 1900 immediately stops wireless communication if it is being performed, and prepares for the transmission of the beacon signal 1701.

As described above, this embodiment can prevent jitter that occurs in fluoroscopic imaging because another wireless communication is performed while a beacon signal is transmitted, and can execute timing synchronization of the present invention in a desired frame cycle.

Sixth Embodiment

In each of the previous embodiments, the wireless communication unit B 621 in the image processing unit 620 including the X-ray generation unit 630 is given the function of an AP or PNC, and transmits the beacon signal in synchronism with the frame cycle. However, the function of an AP or PNC mentioned in the present invention is not an essential function of the wireless communication unit in the image processing unit, and may also be given to the wireless communication unit in the sensor unit or a wireless communication unit in another unit.

In this embodiment, a method of giving the function of an AP or PNC to a wireless communication unit in a sensor unit 610 and determining whether to transmit a beacon signal in accordance with the status of the sensor unit 610 will be explained.

The arrangement of this embodiment will be explained below with reference to FIG. 20. FIG. 20 is an example of a block diagram of this embodiment. The same reference numerals as in FIG. 10 denote the same parts in FIG. 20, and a repetitive explanation will be omitted.

In this embodiment, a timing generation unit 2010 exists in the sensor unit 610, and outputs a timing signal 2011 to a wireless communication unit A 611. The wireless communication unit A 611 receives the timing signal 2011, and transmits a beacon signal. That is, the sensor unit 610 functions as an AP or PNC in this embodiment.

Figure 21B:
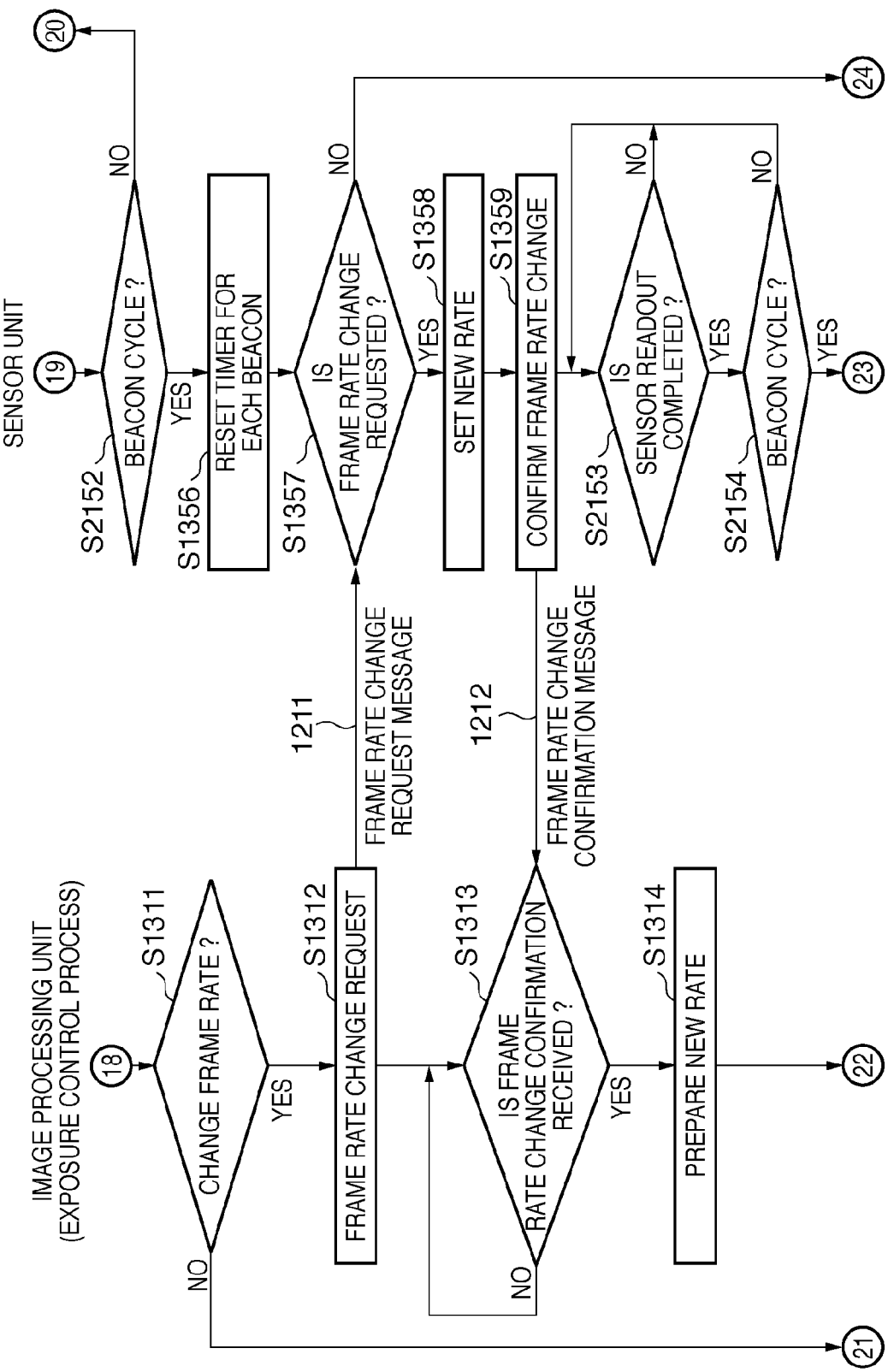
Figure 21C:
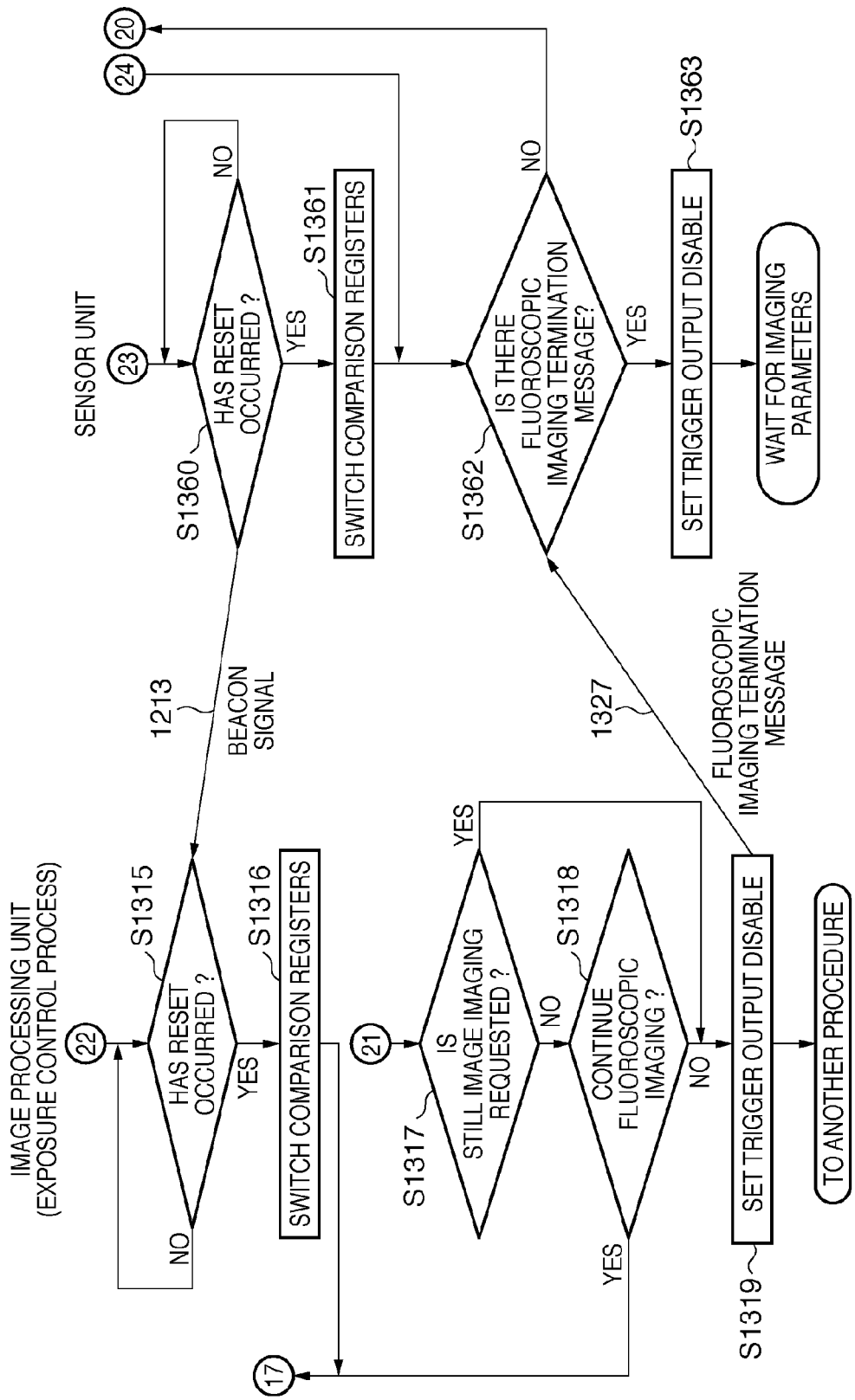

The procedure of performing fluoroscopic imaging in this embodiment will be explained below with reference to FIGS. 21A to 21C. FIGS. 21A to 21C are an example of a flowchart according to this embodiment. The same reference numerals as in FIGS. 13A to 13C denote the same processes in FIGS. 21A to 21C, and only different processes will be explained by attaching reference numerals to them.

Since the sensor unit 610 includes the AP or PNC, the sensor unit 610 changes the beacon interval in step S2150.

In step S2151, a CPU 713 of the sensor unit 610 determines, before transmitting a beacon signal, whether a front-end 712 is reading out data from an X-ray sensor 711. When reading out data by using a line buffer and sending the data being read out line by line by wireless communication, the radio wave condition or disturbance interferes with the wireless communication and causes an error. This prolongs the readout time by, for example, the time required for retransmission. In this case, the next X-ray exposure must be postponed until readout is completed. Therefore, whether readout is completed is determined before beacon transmission. If readout is not completed, the transmission of a beacon signal is delayed. This makes it possible to prevent the start of next exposure and protect the readout data from being destroyed.

If the result of the readout state determination shows that readout is completed, whether the beacon interval has elapsed is determined in step S2152. If the beacon interval has elapsed, the process advances to the next step. The rest of the processing is the same as that explained with reference to FIG. 12.

Even when changing the frame rate, the same processes as above are executed in steps S2152 and S2153.

As described above, this embodiment can reduce synchronization errors between the sensor unit 610 and an image processing unit 620 even when the sensor unit 610 is given the function as an AP or PNC.

Other Exemplary Embodiments

The above-described exemplary embodiments of the present invention can also be achieved by providing a computer-readable storage medium that stores program code of software (computer program) which realizes the operations of the above-described exemplary embodiments, to a system or an apparatus. Further, the above-described exemplary embodiments can be achieved by program code (computer program) stored in a storage medium read and executed by a computer (CPU or micro-processing unit (MPU)) of a system or an apparatus.

The computer program realizes each step included in the flowcharts of the above-mentioned exemplary embodiments. Namely, the computer program is a program that corresponds to each processing unit of each step included in the flowcharts for causing a computer to function. In this case, the computer program itself read from a computer-readable storage medium realizes the operations of the above-described exemplary embodiments, and the storage medium storing the computer program constitutes the present invention.

Further, the storage medium which provides the computer program can be, for example, a floppy disk, a hard disk, a magnetic storage medium such as a magnetic tape, an optical/magneto-optical storage medium such as a magneto-optical disk (MO), a compact disc (CD), a digital versatile disc (DVD), a CD read-only memory (CD-ROM), a CD recordable (CD-R), a nonvolatile semiconductor memory, a ROM and so on.

Further, an OS or the like working on a computer can also perform a part or the whole of processes according to instructions of the computer program and realize functions of the above-described exemplary embodiments.

In the above-described exemplary embodiments, the CPU jointly executes each step in the flowchart with a memory, hard disk, a display device and so on. However, the present invention is not limited to the above configuration, and a dedicated electronic circuit can perform a part or the whole of processes in each step described in each flowchart in place of the CPU.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-029588, filed on Feb. 8, 2008, which is hereby incorporated by reference herein in its entirety.

What is claimed is:

1. A wireless X-ray fluoroscopic imaging system comprising:
an X-ray generation unit configured to perform X-ray exposure for each frame of fluoroscopic imaging;
a sensor unit including a sensor configured to convert X-rays of the X-ray exposure into charge distribution information and output the information as image data; and
an image processing unit configured to designate the exposure by said X-ray generation unit, and receive the image data from said sensor unit,
wherein said sensor unit and said image processing unit communicate with each other via a wireless link,
said sensor unit includes
a first counter configured to be reset and resume counting in response to a beacon signal communicated via the wireless link, and
a unit configured to save a counter value corresponding to a readout trigger offset which defines a time from start of the frame to start of readout of the image data, and
starts the readout when a counter value of said first counter matches the saved counter value corresponding to the readout trigger offset, and transfers the readout image data to said image processing unit via the wireless link, and
said image processing unit includes
a second counter configured to be reset and resume counting in response to the beacon signal of the wireless link, and
a unit configured to save a counter value corresponding to an exposure trigger offset which defines a time from start of the frame to start of the exposure, and
starts the exposure when a counter value of said second counter matches the saved counter value corresponding to the exposure trigger offset.

2. The system according to claim 1, wherein a communication interval of the beacon signal is matched with a frame cycle.

3. The system according to claim 1, wherein
a communication interval of the beacon signal is matched with a value obtained by dividing a frame cycle by a predetermined natural number, and
said first counter and said second counter are reset and resume counting whenever the beacon is transmitted a number of times equal to the natural number.

4. The system according to claim 1, wherein
a communication interval of the beacon signal is matched with a value obtained by multiplying a frame cycle by a predetermined natural number,
said sensor unit starts the readout during a communication internal of the beacon signal whenever the counter value of said first counter matches a counter value corresponding to the frame cycle, even after the counter value of said first counter matches the counter value corresponding to the readout trigger offset, and
said image processing unit starts the exposure during the communication interval of the beacon signal whenever the counter value of said second counter matches the counter value corresponding to the frame cycle, even after the counter value of said second counter matches the counter value corresponding to the exposure trigger offset.

5. The system according to claim 1, wherein
when changing a frame cycle from a first frame cycle to a second frame cycle during fluoroscopic imaging,
said unit which saves the readout trigger offset saves a first readout trigger offset for use in the first frame cycle and a second readout trigger offset for use in the second frame cycle,
said unit which saves the exposure trigger offset saves a first exposure trigger offset for use in the first frame cycle and a second exposure trigger offset for use in the second frame cycle,
one of said sensor unit and said image processing unit changes a communication interval of the beacon signal to the second frame cycle, and
in response to a beacon signal communicated at the changed communication interval, said sensor unit switches the first readout trigger offset to the second readout trigger offset, and said image processing unit switches the first exposure trigger offset to the second exposure trigger offset.

6. The system according to claim 1, wherein when the counter value of one of said first counter and said second counter matches a counter value corresponding to a transfer interruption offset which defines a time from start of the frame to interruption of data transfer in the wireless link, the data transfer in the wireless link is interrupted until a new beacon signal is communicated.

7. The system according to claim 1, wherein said image processing unit includes a wireless communication unit which transmits the beacon signal.

8. The system according to claim 1, wherein said sensor unit includes a wireless communication unit which transmits the beacon signal.

9. The system according to claim 1, wherein a protocol used in the wireless link is a CSMA/CA scheme.

10. An inter-unit synchronization method in a wireless X-ray fluoroscopic imaging system comprising:
an X-ray generation unit configured to perform X-ray exposure for each frame of fluoroscopic imaging;
a sensor unit including a sensor configured to convert X-rays of the X-ray exposure into charge distribution information and output the information as image data; and
an image processing unit configured to designate the exposure by said X-ray generation unit, and receive the image data from said sensor unit,
said sensor unit and the image processing unit communicating with each other via a wireless link,
wherein said sensor unit includes a first counter configured to be reset and resume counting in response to a beacon signal communicated by the wireless link, and save a counter value corresponding to a readout trigger offset which defines a time from start of the frame to start of readout of the image data, and starts the readout when a counter value of said first counter matches the saved counter value corresponding to the readout trigger offset, and transfers the readout image data to said image processing unit via the wireless link, and said image processing unit includes a second counter configured to be reset and resume counting in response to the beacon signal of the wireless link, and saves a counter value corresponding to an exposure trigger offset which defines a time from start of the frame to start of the exposure, and said X-ray generation unit starts the exposure when a counter value of said second counter matches the saved counter value corresponding to the exposure trigger offset.

11. A computer program which is stored in a recording medium and causes a computer to function as a wireless X-ray fluoroscopic imaging system cited in claim 1.

* * * * *